US010557178B2

(12) United States Patent
Cho et al.

(10) Patent No.: US 10,557,178 B2
(45) Date of Patent: Feb. 11, 2020

(54) PROBES FOR IDENTIFYING GEOGRAPHICAL DISTRIBUTION AND MOLECULAR EPIDEMIOLOGY OF VIRAL HEMORRHAGIC SEPTICEMIA VIRUS (VHSV) AND USES THEREOF

(71) Applicant: National Institute of Fisheries Science, Busan (KR)

(72) Inventors: Miyoung Cho, Busan (KR); Myoung Ae Park, Busan (KR); Bo-Young Jee, Busan (KR); Seong Don Hwang, Busan (KR); Kwang Il Kim, Busan (KR); Sang Jung Ahn, Busan (KR)

(73) Assignee: NATIONAL INSTITUTE OF FISHERIES SCIENCE, Busan (KR)

( * ) Notice: Subject to any disclaimer, the term of this patent is extended or adjusted under 35 U.S.C. 154(b) by 0 days.

(21) Appl. No.: 15/578,515

(22) PCT Filed: Aug. 11, 2016

(86) PCT No.: PCT/KR2016/008830
§ 371 (c)(1),
(2) Date: Nov. 30, 2017

(87) PCT Pub. No.: WO2017/030322
PCT Pub. Date: Feb. 23, 2017

(65) Prior Publication Data

US 2018/0155799 A1 Jun. 7, 2018

(30) Foreign Application Priority Data

Aug. 18, 2015 (KR) ........................ 10-2015-0116166

(51) Int. Cl.
*C12Q 1/68* (2018.01)
*C12Q 1/70* (2006.01)

(52) U.S. Cl.
CPC ....... *C12Q 1/701* (2013.01); *C12Q 2600/156* (2013.01)

(58) Field of Classification Search
None
See application file for complete search history.

(56) References Cited

FOREIGN PATENT DOCUMENTS

| | | | |
|---|---|---|---|
| JP | 2001286300 | A | 10/2001 |
| JP | 2013236625 | A | 11/2013 |
| KR | 10-2014-0091944 | A | 7/2014 |
| KR | 10-2015-0028063 | A | 3/2015 |
| WO | 2011046193 | A1 | 4/2011 |

OTHER PUBLICATIONS

Ahn et al. (J. Fish Pathol. 26(3):149-161, 2013) (Year: 2013).*

Petersen et al. (Molecular and Cellular Probes 18 (2004) 117-122) (Year: 2004).*

Marras S.A.E. (2006) Selection of Fluorophore and Quencher Pairs for Fluorescent Nucleic Acid Hybridization probes. In: Didenko V.V. (eds) Fluorescent Energy Transfer Nucleic Acid Probes. Methods in Molecular Biology™, vol. 335. Humana Press, pp. 3-16. (Year: 2006).*

Erali et al. Experimental and Molecular Pathology 85 (2008) 50-58 (Year: 2008).*

Ahn, S. J., et al., "Phylogenetic Analysis of Viral Haemorrhagic Septicaemia Virus (VHSV) Isolates from Asia", "Journal of Fish Pathology", 2013, pp. 149-161; English Abstract Only, vol. 26, No. 3.

Cho, M. Y., et al., "Genetically similar VHSV isolates are differentially virulent in olive flounder *Paralichthys olivaceus*", "Diseases of Aquatic Organisms", Nov. 8, 2012, pp. 105-114, vol. 101.

Dale, O. B., et al., "Outbreak of viral haemorrhagic septicaemia (VHS) in seawater-farmed rainbow trout in Norway caused by VHS virus Genotype III", "Diseases of Aquatic Organisms", Jun. 10, 2009, pp. 93-103, vol. 85.

Dixon, P. F., et al., "Isolation of viral haemorrhagic septicaemia virus from Atlantic herring Clupea harengus from the English Channel", "Diseases of Aquatic Organisms", Aug. 28, 1997, pp. 81-89, vol. 30.

Einer-Jensen, K., et al., "Characterization of Intramolecular Disulfide Bonds and Secondary Modifications of the Glycoprotein from Viral Hemorrhagic Septicemia Virus, a Fish Rhabdovirus", "Journal of Virology", Dec. 1998, pp. 10189-10196, vol. 72, No. 12.

Einer-Jensen, K., et al., "Evolution of the fish rhabdovirus viral haemorrhagic septicaemia virus", "Journal of General Virology", Jan. 7, 2004, pp. 1167-1179, vol. 85.

Elsayed, E., et al., "Isolation of viral haemorrhagic septicaemia virus from muskellunge, Esox masquinongy (Mitchill), in Lake St Clair, Michigan, USA reveals a new sublineage of the North American genotype", "Journal of Fish Diseases", 2006, pp. 611-619, vol. 29.

(Continued)

*Primary Examiner* — Juliet C Switzer
(74) *Attorney, Agent, or Firm* — Hultquist, PLLC; Steven J. Hultquist

(57) ABSTRACT

The present invention relates to a single-nucleotide polymorphism (SNP) for determining genotypes specific to the regions from which VHSV has been isolated, to PNA for identifying same and a method for identifying, by using same, the single-nucleotide polymorphism (SNP) for determining genotypes specific to the regions from which VHSV has been isolated and, more specifically, to PNA and a kit capable of detecting the single-nucleotide polymorphism mutations of C755A and A756G of the VHSV G-protein by using PNA comprising a sequence of SEQ ID NO: 1. The present invention enables an easy, rapid and accurate identification of genotypes specific to the regions from which VHSV has been isolated, by using PNA having an excellent binding affinity to DNA so as to make each genotype exhibit a different melting temperature.

4 Claims, 5 Drawing Sheets
(4 of 5 Drawing Sheet(s) Filed in Color)
Specification includes a Sequence Listing.

(56) References Cited

OTHER PUBLICATIONS

Gagne, N., et al., "Isolation of viral haemorrhagic septicaemia virus from mummichog, stickleback, striped bass and brown trout in eastern Canada", "Journal of Fish Diseases", 2007, pp. 213-223, vol. 30.
Isshiki, T., et al., "An outbreak of VHSV (viral hemorrhagic septicemia virus) infection in farmed Japanese flounder *Paralichthys olivaceus* in Japan", "Diseases of Aquatic Organisms", Nov. 8, 2001, pp. 87-99, vol. 47.
Kim, S.-M., et al., "Genetic relationship of the VHSV (Viral Hemorrhagic Septicemia Virus) isolated from cultured olive flounder, *Paralichthys olivaceus* in Korea", "Journal of Fish Pathology", 2003, pp. 1-12; English Abstract Only, vol. 16, No. 1.
Kim, S.-H., et al., "Interchange of L polymerase protein between two strains of viral hemorrhagic septicemia virus (VHSV) genotype IV alters temperature sensitivities in vitro", "Virus Research", 2015, pp. 203-206, vol. 195.
Kim, S.-M., et al., "Detection of Viral Hemorrhagic Septicemia Virus (VHSV) in Wild Marine Fishes in the Coastal Region of Korea", "Journal of Fish Pathology", 2004, pp. 1-10; English Abstract Only, vol. 17, No. 1.
Kim, W.-S., et al., "An outbreak of VHSV (viral hemorrhagic septicemia virus) infection in farmed olive flounder *Paralichthys olivaceus* in Korea", "Aquaculture", 2009, pp. 165-168, vol. 296.
Lopez-Vasquez, C., et al., "Development of a rapid, sensitive and non-lethal diagnostic assay for the detection of viral haemorrhagic septicaemia virus", "Journal of Virological Methods", 2006, pp. 167-174, vol. 133.
Lumsden, J. S., et al., "Mortality event in freshwater drum Aplodinotus grunniens from Lake Ontario, Canada, associated with viral haemorrhagic septicemia virus, Type IV", "Diseases of Aquatic Organisms", Jun. 29, 2007, pp. 99-111, vol. 76.
Meyers, T. R., et al., "Viral Hemorrhagic Septicemia Virus in North America", "Annual Review of Fish Diseases", 1995, pp. 3-24, vol. 5.
Mortensen, H. F., et al., "Isolation of viral haemorrhagic septicaemia virus (VHSV) from wild marine fish species in the Baltic Sea, Kattegat, Skagerrak and the North Sea", "Virus Research", 1999, pp. 95-106, vol. 63.
Nishizawa, T., et al., "Genetic relatedness among Japanese, American and European isolates of viral hemorrhagic septicemia virus (VHSV) based on partial G and P genes", "Diseases of Aquatic Organisms", Mar. 11, 2002, pp. 143-148, vol. 48.
Schlotfeldt, H.-J., et al., "Occurance of Viral Haemorrhagic Septicaemia in Turbot (*Scophthalmus maximus*)—a Natural Outbreak", "Bulletin of the European Association of Fish Pathologists", 1991, pp. 105-107, vol. 11, No. 3.
Schutze, H., et al., "Complete Genomic Sequence of Viral Hemorrhagic Septicemia Virus, a Fish Rhabdovirus", "Virus Genes", 1999, pp. 59-65, vol. 19, No. 1.
Snow, M., et al., "Analysis of the nucleoprotein gene identifies distinct lineages of viral haemorrhagic septicaemia virus within the European marine environment", "Virus Research", 1999, pp. 35-44, vol. 63.
Snow, M., et al., "Genetic population structure of marine viral haemorrhagic septicaemia virus (VHSV)", "Diseases of Aquatic Organisms", Oct. 21, 2004, pp. 11-21, vol. 61.
Takano, R., et al., "Isolation of viral haemorrhagic septicaemia virus (VHSV) from wild Japanese flounder, *Paralichthys olivaceus*", "Bulletin of the European Association of Fish Pathologists", 2000, pp. 186-192, vol. 20, No. 5.
Thiery, R., et al., "Phylogenetic analysis of viral haemorrhagic septicaemia virus (VHSV) isolates from France (19711999)", "Diseases of Aquatic Organisms", Nov. 7, 2002, pp. 29-37, vol. 52.
Zwillenberg, L. O., et al., "Electron Microscopy of the Virus of Viral Haemorrhagic Septicaemia of Rainbow Trout (*Egtved virus*)", "Archives of Virology", Feb. 1965, pp. 1-19, vol. 17, No. 1.
Note: For the non-patent literature citations that no month of publication is indicated, the year of publication is more than 1 year prior to the effective filing date of the present application.
Hopper, K., "The Isolation of VHSV From Chinook Salmon at Glenwood Springs, Orcas Island, Washington", "Fish Health Section: News Letter", 1989, pp. 1-10, vol. 17, No. 2, Publisher: Washington Department of Fisheries.
Jensen, N.J., et al., "The Ulcus-Syndrome in Cod (*Gradus morhua*) III. A preliminary virological report", "Nord. Vet.-Med.", 1979, pp. 436-442, vol. 31.

* cited by examiner

The 741-760 region of VHSV G protein (SEQ ID NO: 44)

Korea: A A
USA/ Canada/ Japan: C G
Europe: C A

Korea — 755A 756G — Perfect match

USA — 755C 756G — Single mismatch

Europe — 755C 756G — Double mismatch

| | | |
|---|---|---|
| Initial denaturation | 95 °C | 5 min |
| 40 cycles | 95 °C | 30 sec |
| | 56 °C | 45 sec |
| | 74 °C | 30 sec |
| Re-denaturation | 95 °C | 5 min |
| Probe binding | 85 °C | 30 sec |
| | 75 °C | 30 sec |
| | 65 °C | 30 sec |
| | 55 °C | 30 sec |
| | 45 °C | 30 sec |
| | 35 °C | 30 sec |
| | 25 °C | 30 sec |
| Melt curve | 25 °C to 85 °C | Increment 1.0°C, 10 sec; plate read |

FIG. 8

| Origin | Melting Temperature | Type |
|---|---|---|
| Korean | 69 °C | Perfect match |
| US, CA, JPN, CHI | 58 °C | Single mismatch |
| EUR | 49 °C | Double mismatch |
| NTC | - | - |

SEQUENCE LISTING

```
<160> NUMBER OF SEQ ID NOS: 44

<210> SEQ ID NO 1
<211> LENGTH: 14
<212> TYPE: DNA
<213> ORGANISM: Artificial Sequence
<220> FEATURE:
<223> OTHER INFORMATION: VHSV-1

<400> SEQUENCE: 1

gcatgcaagg tgac                                                14


<210> SEQ ID NO 2
<211> LENGTH: 22
<212> TYPE: DNA
<213> ORGANISM: Artificial Sequence
```

-continued

<220> FEATURE:
<223> OTHER INFORMATION: VHSV-F1

<400> SEQUENCE: 2
gatcacaggg tggtcaaggc aa 22

<210> SEQ ID NO 3
<211> LENGTH: 21
<212> TYPE: DNA
<213> ORGANISM: Artificial Sequence
<220> FEATURE:
<223> OTHER INFORMATION: VHSV-R1

<400> SEQUENCE: 3
tcccccaggt cggtcttgat c 21

<210> SEQ ID NO 4
<211> LENGTH: 1524
<212> TYPE: DNA
<213> ORGANISM: Artificial Sequence
<220> FEATURE:
<223> OTHER INFORMATION: DQ401186_CAN

<400> SEQUENCE: 4
atggaatgga atactttttt cttggtgatt ctgatcatca tcataaaaag caccacatca 60
cagatcactc aacgacctcc ggtcgagaac atctcaacat accatgcaga ctgggacact 120
ccactgtata ctcacccttc caactgcaga aaaaactcct ttgttccgat tcggccagct 180
caactcaggt gtccccatga gttcgaggac acaaacaagg gcttggtctc tgtcccagcc 240
cagatcatcc atcttccgtt atcagtcacc agcgtctcag cagtcgcaaa tggccactac 300
ctacacagag tgacctaccg ggtcacctgc tcaaccagtt tctttggagg acaaaccatt 360
gaaaaaacca tcctggaggc aaagctgtcc cgtcaagagg ccaccaatga ggccggcaag 420
gatcacgagt accctttctt ccccgaacct tcctgcatct ggatgaagga caatgtccac 480
aaggacataa cccactatta caagacccca aagacagtgt ccattgatct ctacagtaga 540
aagtttctaa accctgactt catagagggg gtttgtacaa catcaccctg cccaacccac 600
tggcaaggag tctactggat cggcgctaca cctcaggccc attgccctac ctcagaaacg 660
cttaaggggc atctgttcac caggacacat gatcacaggg tggtcaaggc aatcgttgcg 720
ggtcaccacc cctgggggct cacaatggca tgcacggtga cattttgtgg gacagaatgg 780
atcaggaccg acctgggga ccttattcag gtgacagggc aggggggagc gaagaaactg 840
tctccaaaga agtgtgtcaa caccgacgtt cagatgaggg gagccacaga cgacttctct 900
tatcttaacc atctcattac caacatggct caaagaactg agtgcctgga cgcccacagt 960
gatatcactg cctctgggaa gatatcccct tttctcctct caaagtttcg tcctagtcac 1020
ccggggccgg gcaaggcaca ttatctcctt gatggccaga tcatgcgagg tgagtgtgat 1080
tacgaggccg tggtcagcat caactacaac agtgctcagt acaagacggt aaacaacacc 1140
tggaaaccat ggaatcggat agacaacaac actgacgggt atgatggaat gatattcggg 1200
gacaaattga tcatcccaga catcgagaaa taccagagca tctatgacag cggaatgctt 1260
gttcaaagaa acctggtgga aattccccat ccgagcattg tgttcgtctc caacacatct 1320
gatctctcca ctaaccacat ccacaccaat ctaattcctt cggattggtc attcaattgg 1380
agtctttggc cgtcactatc aggaatgggg gtagtgggag gggccttcct tctgctcgtg 1440
ctctgctgtt gctgcagggc atctccccct cttccgagtt acgggattcc gatgcagcag 1500
ttctccagaa gccagatggt ctga 1524

<210> SEQ ID NO 5
<211> LENGTH: 1524
<212> TYPE: DNA
<213> ORGANISM: Artificial Sequence
<220> FEATURE:
<223> OTHER INFORMATION: EF079899_CAN

<400> SEQUENCE: 5
atggaatgga acactttttt cttggtgatt ctgataatca tcataaaaag caccacatca 60
cagatcactc aacgacctcc ggtcgagaat atctcaacat accatgcaga ttgggacact 120
ccactgtata ctcacccttc caactgtaga aaagactcct ttgtaccgat tcgaccagct 180
caactcaggt gtcctcatga attcgaggac ataaacaagg gcttggtctc tgtcccaact 240
cagatcatac atcttccgct atcagtcacc agcgtctcag cagttgcaag tggacactac 300
ctacacagag tgacctaccg agtcacctgc tcaaccggtt tttttggagg acaaaccatt 360
gagaagacca tcctggaagc aaagctgtcc cgtcaagagg ccgccaatga ggccggcaag 420
gatcacgagt acccgttctt ccccgaacct tcctgcatct ggatgaagga caatgtccac 480
aaggacataa cccactatta caagacccca aagacagtgt ccatcgatct ctacagtaga 540
aagtttctaa accctgactt catagagggg gtctgtacaa catcaccctg cccaactcac 600
tggcaaggag tctactggat cggcgccaca cctcaggccc attgccccac ctcagaaacg 660
cttgaggggc atctgttcac caggacacat gatcacaggg tggtcaaggc aatcgtggca 720
ggtcaccacc cctgggggct cacaatggca tgcacggtga cattttgtgg gacagaatgg 780
atcaagaccg acctgggga ccttattcag gtgacaggac agggggagc gaagaaactg 840 tctccaagga agtgtgtcaa caccaacatt cagatgaggg gagccacaga cgacttctct 900
taccttaacc atctcatcac caacatggct caaagaactg agtgcctgga cgcccacagt 960
gatatcactg cctccgggaa gatctcctct tttctcctct caaagtttcg tcctagtcac 1020
ccggggccgg gcaaggcaca ttatctcctt gatggccaga tcatgcgagg tgagtgtgac 1080
tatgaggccg tggtcagcat caactacaac agtgctcagt acaagacggt aaacaacacc 1140
tggaaatcat ggaatcggat agacaacaac actgacgggt atgatggaat gatattcggg 1200
gacaaattga tcatcccaga catcgagaaa taccagagca tctatgacag tggaatgctc 1260
gttcaaagga acctggtgga aattccccat ctgagtattg tgttcgtctc caacacatct 1320
gatctctcca ctaaccacat ccacaccaat ctaattcctt cggattggtc gttcaattgg 1380
agtctttggc cgtcactgtc aggaatgggg gtagtgggag gggccttcct tctactagtg 1440
ctctgctgtt gctgcaaggc atctcctcct cttccgagtt acgggattcc gatgcagcag 1500
ttctccagaa gccagatggt ctga 1524

<210> SEQ ID NO 6
<211> LENGTH: 1524
<212> TYPE: DNA
<213> ORGANISM: Artificial Sequence
<220> FEATURE:
<223> OTHER INFORMATION: EF079896_CAN

<400> SEQUENCE: 6
atggaatgga atactttttt cttggtgatt ctgataatca tcataaaaag caccacatca 60
cagatcactc aacgacctcc ggtcgagaat atctcaacat accatgcaga ttgggacact 120
ccactgtata ctcacccttc caactgtaga aaagactcct ttgtaccgat tcgaccagct 180

```
caactcaggt gtcctcatga attcgaggac ataaacaagg gcttggtctc tgtcccaact    240
cagatcatac atcttccgct atcagtcacc agcgtctcag cagttgcaag tggccactac    300
ctacacagag tgacctaccg agtcacctgc tcaaccggtt tttttggagg acaaaccatt    360
gagaagacca tcctggaagc aaagctgtcc cgtcaagagg ccgccaatga ggccggcaag    420
gatcacgagt acccgttctt ccccgaacct tcctgcatct ggatgaagga caatgtccac    480
aaggacataa cccactatta caagacccca aagacagtgt ccatcgatct ctacagtaga    540
aagtttctaa accctgactt catagagggg gtctgtacaa catcaccctg cccaacccac    600
tggcaaggag tctactggat cggcgccaca cctcaggccc attgccccac ctcagaaacg    660
cttgaggggc atctgttcac caggacacat gatcacaggg tggtcaaggc aatcgtggca    720
ggtcaccacc cctgggggct cacaatggca tgcacggtga cattttgtgg gacagaatgg    780
atcaagaccg acctggggga ccttattcag gtgacaggac agggggggagc gaagaaactg    840
tctccaagga agtgtgtcaa caccaacatt cagatgaggg gagccacaga cgacttctct    900
taccttgacc atctcatcac caacatggct caaagaactg agtgcctgga cgcccacagt    960
gatatcactg cctctgggaa gatctcctct tttctcctct caaagtttcg tcctagtcac   1020
ccggggccgg gcaaggcaca ttatctcctt gatggccaga tcatgcgagg tgagtgtgac   1080
tatgaggccg tggtcagcat caactacaac agtgctcagt acaagacggt aaacaacacc   1140
tggaaatcat ggaatcggat agacaacaac actgacgggt atgatggaat gatattcggg   1200
gacaaattga tcatcccaga catcgagaaa taccagagca tctatgacag tggaatgctc   1260
gttcaaagga acctggtgga aattccccat ctgagtattg tgttcgtctc caacacatct   1320
gatctctcca ctaaccacat ccacaccaat ctaattcctt cggattggtc gttcaattgg   1380
agtctttggc cgtcactgtc aggaatgggg gtagtgggag gggccttcct tctactagtg   1440
ctctgctgtt gctgcaaggc atctcctcct cttccgagtt acgggattcc gatgcagcag   1500
ttctccagaa gccagatggt ctga                                            1524
```

<210> SEQ ID NO 7
<211> LENGTH: 1524
<212> TYPE: DNA
<213> ORGANISM: Artificial Sequence
<220> FEATURE:
<223> OTHER INFORMATION: HQ453209_CAN

<400> SEQUENCE: 7

```
atggaatgga atactttttt cttggtgatt ctgatcatca tcataaaaag caccacatca     60
cagatcactc aacgacctcc ggtcgagaat atctcaacat accatgcaga ctgggacact    120
ccactgtata ctcacccctc caactgcaga aaagactcct ttgttccgat tcggccagct    180
caactcaggt gtcctcatga gttcgaggac ataaacaagg gcttggtctc tgtcccaact    240
cagatcatac atcttccgtt atcagtcacc agcgtctcag cagtcgcacg tggccactac    300
ctacacagag tgacctaccg ggtcacctgc tcaaccggtt tctttggagg acaaaccatt    360
gaaaagacca tcctggaagc aaagctgtcc cgtcaagagg ccaccaatga ggccggcaag    420
gatcacgagt acccgttctt ccccgaacct tcctgcatct ggatgaagga caatgtccac    480
aaggacataa cccactatta caagacccca aagacagtgt ccatcgatct ctacagtaga    540
aagtttctaa accctgactt catagagggg gtctgtacaa catcaccctg tccaacccac    600
tggcaaggag tctactggat cggcgccaca cctcaggccc attgccccac ctcagaaacg    660
```

-continued

```
cttgaggggc atctgttcac caggacacat gatcacaggg ttgtcaaggc aatcgtagcg    720

ggtcaccacc cctggggact cacaatggca tgcacggtga cattttgtgg ggcagaatgg    780

atcaagaccg acctgggga ccttattaag gtgacaggac agggggggc gaagaaactg    840

tctccaagga agtgtgtcaa caccgacatt cagatgaggg gagccacaga cgacttctct    900

taccttaacc atctcatcac caacatggct caaaggactg agtgcctgga cgcccacagt    960

gatatcactg cctctgggaa gatctcctct tttctcctct caaagtttcg tcccagtcac   1020

ccggggccgg gcaaggcaca ctatctcctt gatggccaga tcatgcgagg tgagtgtgat   1080

tatgaggccg tggtcagcat caactacaac agtgctcagt acaagacggt aaacaacacc   1140

tggaaatcat ggaatcggat agacaacaac accgacgggt atgatggaat gatattcggg   1200

gacaaattga tcatcccaga catcgagaag taccagagca tctatgacag tggaatgctt   1260

gttcaaagga acctggtgga aattccccat ccgagtattg tgttcgtctc caacacatct   1320

gatctctcca ctaaccacat ccacaccaat ctaattcctt cggattggtc attcaattgg   1380

agtctttggc cgtcactatc aggaatgggg gtaatgggag gggccctcct tctactagtg   1440

ctctgctgtt gctgcaaggc atctcctcct attccgagtt acgggattcc gatgcagcag   1500

ttctccagaa acccgatggt ctga                                          1524
```

```
<210> SEQ ID NO 8
<211> LENGTH: 1524
<212> TYPE: DNA
<213> ORGANISM: Artificial Sequence
<220> FEATURE:
<223> OTHER INFORMATION: AY546612_DK

<400> SEQUENCE: 8
```

```
atggaatgga atactttctt cttggtgatc ttgatcatca tcataaagag caccacacca     60

cagatcactc aacgacctcc ggttgaaaac atctcgacgt accatgcaga ttgggacact    120

ccgctataca ctcatccctc caactgcagg gacgattcct ttgtcccgat tcgaccagct    180

caactcaggt gtcctcatga atttgaggac ataaacaggg gactggtttc cgtcccaacc    240

aagatcatcc atctcccgct atcagtcacc agcgtctccg cagtagcgag cggccactac    300

ctgcacagag tgacttatcg agtcacctgt tcgaccagct tctttggagg gcaaaccatt    360

gaaaagacca tcttggaggc gaaactgtct cgtcaggagg ccacagacga ggcaagcaag    420

gaccacgagt acccgttctt ccctgaaccc tcctgcatct ggatgaaaaa caatgtccat    480

aaggacataa ctcactatta caagacccca aaaacagtat cggtggatct ctacagcagg    540

aaatttctca accctgattt catcgaaggg gtctgcacaa cctcgccctg tcaaactcat    600

tggcagggag tctattgggt cggcgccaca cccaaagccc attgccccac gtcggaaaca    660

ctagaaggac acctgttcac caggacccat gatcacaggg tggtcaaggc aattgtggca    720

ggccatcatc cctggggact cacaatggca tgcacagtga cattctgcgg ggaagactgg    780

atcaagactg acctgggaga cctgatccag gtgacaggac cggggggcac ggggaaactg    840

actccaaatg agtgtgtcaa cactgatgtc cagatgaggg gggcaacaga cgacttttct    900

tatctcaacc atctcatcac caacatggct caaagaaccg agtgcctaga tgcccatagt    960

gatatcaccg cttctgggaa agtgtcctca tttctcctct caaagtttcg tcccagccac   1020

cctggacccg gcaaggcaca ctatcttcta gacggtcaaa tcatgcgagg tgactgtgac   1080

tatgaggcag tagtcagcat caactacaac agcgctcaat acaagacggt gaacaacaca   1140

tggaaatcat ggaaacgggt ggacaacaac acagacgggt acgatgggat gatatttggg   1200
```

gacaaattga tcatcccgga catcgagaag tatcagagtg tctatgacag tggaatgctc 1260
gttcaaagaa accttgtgga agtccctcat ctgagcattg tgtttgtctc caacacatct 1320
gatctttcca ctaatcacat ccacaccaac ctaatccctt cggattggtc attccactgg 1380
agtctttggc cctcattgtc tgggatgggg gttgtgggag gggccttcct tctactggtg 1440
ctttgctgtt gctgcaaggc gtcccctcca actccaaact acgggattcc gatgcagcag 1500
ttctccagaa gtcagatggt ctga 1524

<210> SEQ ID NO 9
<211> LENGTH: 1524
<212> TYPE: DNA
<213> ORGANISM: Artificial Sequence
<220> FEATURE:
<223> OTHER INFORMATION: AF345857_DK

<400> SEQUENCE: 9
atggaatgga ataccttttc cttggtgatc ttgatcatca tcttaaagag caccacacca 60
cagatcactc aacgacctcc ggtcgaaaac atctcgacgt accatgcaga ttgggacact 120
ccgctataca ctcatcccgc caactgcagg gaagattcct ttgtcccgat tcgaccagct 180
caactcaggt gtcctcatga atttgaagac ataaacaagg gactggtttc cgtcccaact 240
cagatcatcc atctcccgct atcagtcacc agcgtctccg cagtagcgag tggccactac 300
ctgcacagag tgacttatcg cgtaacctgt tcgaccagct tctttggagg gcaaaccatc 360
gaaaagacca tcttggaggc gaaattgtct cgtcaggagg ccacaaacga ggcaagcaag 420
gatcacgagt acccgttctt ccctgaaccc tcctgcatct ggatgaaaaa caatgtccat 480
aaggacataa ctcactatta caagacccca aaaacagtat cggtggatct ctacagcagg 540
aaatttctca accctgattt catagagggg gtctgcacaa cctcgccctg tcaaactcat 600
tggcagggag tctattgggt cggtgccaca cctacagccc attgccccga gtcggaaaca 660
ctagaaggac acctgttcac caggacccat gatcacaggg tggtcaaggc aattgtggca 720
ggccatcatc cctggggact cacaatggca tgcacagtga cattctgcgg gacagaatgg 780
atcaagaccg acctggggga cctgatcaag gtgacaggac cgggggcgc gaggaaactg 840 actccaaaaa aatgtgtcaa tgccgatatc cagatgaggg gggcaacaga cgacttttct 900
tatctcaacc atctcatcac caacatggct caaagaaccg agtgcctaga tgcccatagt 960
gatatcaccg cttcggggaa aatatcctca tttctcctct caaagtttcg tcccagccac 1020
cctggacccg gcaaggcaca ctatcttctc gacggtcaaa tcatgcgagg tgactgtgac 1080
tatgaggcag tagtcagcat caactacaat agtgctcgat acaagacggt gaacaacaca 1140
tggaaatcat ggaaacgggt aggcaacaac acagacgggt acgatgggat gatatttggg 1200
gacaaattga tcatcccgga catcgagaag tatcagagtg tctatgacag tggaatgctc 1260
gttcaaagaa accttgtgga agtccctcat ctgagcattg tgtttgtctc caacacatcc 1320
gatctttcca ctaatcgcat ccacaccaac ctaatccctt cggattggtc attcaactgg 1380
agtctttggc catcattatc tgggatgggg gttgtgggag gggccttcct tctactggta 1440
ctctgctgtt gctgcaaggc gtcccctcct attccaaatt acgggattcc gatgcagcag 1500
ttctccagaa gtcagacggt ctaa 1524

<210> SEQ ID NO 10
<211> LENGTH: 1524
<212> TYPE: DNA

<213> ORGANISM: Artificial Sequence
<220> FEATURE:
<223> OTHER INFORMATION: Z93412_DK

<400> SEQUENCE: 10

```
atggaatgga atactttttt cttggtgatc ttgatcatca tcataaagag caccacacca     60
cagatcactc aacgacctcc ggtcgaaaac atctcgacgt accatgcaga ttgggacact    120
ccgctctaca ctcatccctc caactgcagg gaagattcct ttgtcccgat tcgaccagct    180
caactcaggt gtcctcatga atttgaagac ataaacaagg gactggtctc cgtcccaact    240
cagatcatcc atctcccgct atcagtcacc agcgtctccg cagtagcgag tggccactac    300
ctgcacagag tgacttatcg agtcacctgt tcgaccagct tctttggagg acaaaccatc    360
gaaaagacca tcttggaggc gaaattgtct cgtcaggagg ccacaaacga ggcaagcaag    420
gatcacgagt acccgttctt ccctgaaccc tcctgcatct ggatgaaaaa caatgtccat    480
aaggacataa ctcactatta caagacccca aaaacagtat cggtggatct ctacagcagg    540
aaatttctca accctgattt catagagggg gtttgcacaa cctcgccctg tcaaactcat    600
tggcagggag tctattgggt cggtgccaca cctaaagccc attgccccac gtcggaaaca    660
ctagggggac acctgttcac caggacccat gatcacaggg tggtcaaggc aattgtggca    720
ggccatcatc cctggggact cacaatggca tgcacagtga cattctgcgg gacagactgg    780
atcaagaccg acctggggga cctgatcaag gtgacaggac cgggggcgc gaggaaactg    840
actccaaaaa agtgtgtcaa tgccgacatc cagatgaggg gggcaacaga cgacttttct    900
tatctcaacc atctcatcac caacatggct caaagaaccg agtgcctaga tgcccatagt    960
gatatcaccg cttctgggaa aatatcctca tttctcctct caaagtttcg tcccagccac   1020
cctggacccg gcaaggcaca ctatcttctc gacggtcaaa tcatgcgagg tgactgtgac   1080
tatgaggcag tagtcagcat caactacaat agcgctcaat acaagacggt gaacaacaca   1140
tggaaatcat ggaaacgggt agacaacaac acagacgggt acgatgggat gatatttggg   1200
gacaaattga tcatcccgga catcgagaag tatcagagtg tctatgacag tggaatgctc   1260
gttcaaagaa accttgtgga agtccctcat ctgagcattg tgtttgtctc caacacatcc   1320
gatctttcca ctaatcacat ccaaaccaac ctaatccctt cggattggtc attcaactgg   1380
agtctttggc catcattatc tgggatgggg gttgtgggag gggccctctc tctactggta   1440
ctctgctgtt gctgcaaggc gtcccctcct attccaaatt acgggattcc gatgcagcag   1500
ttctccagaa gtcagacggt ctga                                          1524
```

<210> SEQ ID NO 11
<211> LENGTH: 1524
<212> TYPE: DNA
<213> ORGANISM: Artificial Sequence
<220> FEATURE:
<223> OTHER INFORMATION: GQ292534_Slo

<400> SEQUENCE: 11

```
atggaatgga acactttttt cttggtgatc ttgatcatca tcataaagag caccacacca     60
cagatcactc aacgacctcc ggtcgaaaac atctcgacgt accatgcaga ctgggacact    120
ccgctataca ctcatccctc cagctgcagg gacgattcct ttgtcccgat tcgaccggct    180
caactcaggt gtcctcatga atttgaagac ataaacaagg gactggtttc cgtcccaacc    240
aggatcatcc atctcccgct atcagtcacc agcgtctccg cagtagcgag tggccactac    300
ctgcacaggg tgacttatcg agtcacctgt tcgaccggct tctttggagg gcaaaccatc    360
```

gaaaagacca tcttggaggc gaaactgtcc cgtcaggagg cctcagacga ggcaagcaag 420
gatcacgagt acccgttctt ccctgaaccc tcctgcatct ggatgaagga caatgtccat 480
aaggacataa ctcactatta caagacccca aaaaccgtat cggtggatct ctacagcagg 540
aaatttctca accctgattt catagagggg gtttgcacaa cctcgccctg tcaaactcac 600
tggcagggag tctattgggt cggcgacaca cccaaagccc attgccccac gccagaaaca 660
ctagaaggac acctgttcac caggacccac gatcacaggg tggtcaaggc aattgtggca 720
ggccatcatc cctggggact cacaatggca tgcacggtga cattctgcgg gggagcatgg 780
atcaagaccg acctggggga cctgatccag gtgacaggac cggagggcac gaggaaactg 840
actccaaaca agtgtgtcaa caccgatgtc cagatgaggg gggcaacaga cgacttctct 900
tatctcaacc atctcatcac caacatggct caaagaaccg agtgcctaga tgcccacagt 960
gatatcaccg cttctgggaa agtatcccca tttctcctct caaagtttcg tcccagccac 1020
cctgggcctg gcaaggcaca ctatcttctc gacggccaaa tcatgcgagg tgactgtgac 1080
tatgaggcag tggtcagcat caactacaat agcgctcaat acaagacggt gaacaacaca 1140
tggaaatcat ggaaacgggt ggacaacaac acagatgggt acgatgggat gatatttggg 1200
gacaaattga tcatcccgga catcgaaaag tatcagagtg tctatgacag tggaatgctc 1260
gttcaaagaa accttgtgga agtccctcat ctgagcattg tgttcgtctc caacacatct 1320
gacctttcca ctaatcacat ccacaccaac ctaatccctt cggattggtc attcaactgg 1380
agtctttggc catcattatc ggggatgggg gttgtgggag gggccctcct tctactagta 1440
ctctgctgtt gctgcaaggc gccccctccc attccaaatt acgggattcc gatgcagcag 1500
ttctccagaa gtcagatggt ctga 1524

<210> SEQ ID NO 12
<211> LENGTH: 1524
<212> TYPE: DNA
<213> ORGANISM: Artificial Sequence
<220> FEATURE:
<223> OTHER INFORMATION: Y18263_GER

<400> SEQUENCE: 12
atggaatgga acacttttttt cttggtcatc ttgatcatca tcataaagag caccacacca 60
cagatcactc aacgacctcc ggtcgaaaac atctcgacgt accatgcaga ttgggacact 120
ccgctataca ctcatccctc caactgcagg gacgattcct ttgtcccgat tcgaccagct 180
caactcaggt gtcctcatga atttgaagac ataaacaagg gactggtctc cgtcccaacc 240
aagatcatcc atctcccgct atcagtcacc agcgtctccg cagtcgcgag tggccactac 300
ctgcacagag tgacttatcg agtcacctgt tcgaccagct tctttggagg gcaaaccatt 360
gaaaagacca tcttagaggc gaaactgtct cgtcaggagg ccacagacga ggcaagcaag 420
gatcacgagt acccgttctt ccctgaaccc tcctgcatct ggatgaaaaa caatgtccat 480
aaggacataa ctcactatta caagacccca aaaacagtat cggtggatct ctacagcagg 540
aaatttctca accctgattt catagagggg gtttgcacaa cctcgccctg tcaaactcat 600
tggcagggag tctattgggt cggtgccaca cccaaagccc attgccccac gtcggaaaca 660
ctagaaggac acctgttcac caggacccat gatcacaggg tggtcaaggc aattgtggca 720
ggccatcatc cctggggact cacaatggca tgcacagtga cattctgcgg ggcagaatgg 780
atcaagactg acctgggaga cctgatccag gtaacaggac cggggggcac ggggaaactg 840

-continued

```
actccaaaga agtgtgtcaa tgctgatgtc cagatgaggg gggcaacaga tgacttttct    900

tatctcaacc atctcatcac caacatggct caaagaaccg agtgcctaga tgcccatagt    960

gatatcaccg cttctgggaa aatatcctca tttctcctct caaagtttcg tcccagccac   1020

cctggacccg gcaaggcaca ctatcttctc aacggtcaaa tcatgcgagg tgactgtgac   1080

tatgaggcag tagtcagcat caactacaac agcgctcaat acaagacagt gaacaacaca   1140

tggaaatcat ggaaacgggt agacaacaac acagacgggt acgatgggat gatatttggg   1200

gacaaattga tcatcccgga catcgagaag tatcagagtg tctatgacag tggaatgctc   1260

gttcaaagaa accttgtgga agtccctcat ctgagcattg tgtttgtctc caacacatct   1320

gatctttcca ctaatcacat ccacaccaac ctaatccctt cggattggtc attccactgg   1380

agtatttggc cctcattatc tgggatgggg gttgtgggag gggccttcct tctactggta   1440

ctctgctgtt gctgcaaggc gtcccctccc attccaaatt acgggattcc gatgcagcag   1500

ttctccagaa gtcagacggt ctga                                          1524
```

```
<210> SEQ ID NO 13
<211> LENGTH: 1524
<212> TYPE: DNA
<213> ORGANISM: Artificial Sequence
<220> FEATURE:
<223> OTHER INFORMATION: Z93414_DK

<400> SEQUENCE: 13
```

```
atggaatgga atactttttt cttggtgatc ttgatcatca tcataaagag caccacacca     60

cagatcactc aacgacctcc ggtcgaaaac atctcgacgt accatgcaga ttgggacact    120

ccgctataca ctcatccctc caactgcagg gaagattcct ttgtcccgat tcgaccagct    180

caactcaggt gtcctcatga atttgaagac ataaacaagg gactggtttc cgtcccaact    240

cagatcatcc atctcccgct atcagtcacc agcgtctccg cagtggcgag tggccactac    300

ctgcacagag tgacttatcg agtcacctgt tcgaccagct tctttggagg gcaaaccatc    360

gaaaagacaa tcttggaggc gaaattgtct cgtcaggagg ccacaaacga ggcaagcaag    420

gatcacgagt acccgttctt ccctgaaccc tcctgcatct ggatgaaaaa caatgtccat    480

aaggacataa ctcactatta caagacccca aaaacagtat cggtggatct ctacagcagg    540

aaatttctca accctgattt catagagggg gtttgcacaa cctcgccctg tcaaactcat    600

tggcagggag tctattgggt cggtgccaca cctacagccc attgccccac gtcggaaaca    660

ctagaaggac acctgttcac caggacccat gatcacaggg tggtcaaggc aattgtggca    720

ggccatcatc cctggggact cacaatggca tgcacagtga cattttgcgg gacagaatgg    780

atcaagaccg acctggggga cctgatccag gttacaggac cggggggcgc gaggaaactg    840

actccaaaaa agtgtgtcaa taccgatatc cagatgaggg gggcaacaga cgacttttct    900

tatctcaacc atctcatcac caacatggct caaagaaccg agtgcctaga tgcccatagt    960

gatatcaccg cttctgggaa aatatcctca tttctcctct caaagtttcg tcccagccac   1020

cctggacccg gcaaggcaca ctatcttctc gacggtcaaa tcatgcgagg tgactgtgac   1080

tatgaggcag tagtcagcat caactacaat agcgctcaat acaagacggt gaacaacaca   1140

tggaaatcat ggaaaagggt agacaacaac acagacgggt acgatgggat gatatttggg   1200

gacaaattga tcatcccgga catcgagaag tatcagagtg tctatgacag tggaatgctc   1260

gttcaaagaa accttgtgga agtccctcat ctgagcattg tgtttgtctc caacacatct   1320

gatctttcca ctaatcacat ccacaccaac ctaatccctt cggattggtc attcaactgg   1380
```

agtctttggc catcattatc tgggatgggg gttgtgggag gggccttcct tctgctggta 1440
ctctgctgtt gctgcaaggc atcccctcct attccaaact acgggattcc gatgcagcag 1500
ttctccagaa gccagatggt ctga 1524

<210> SEQ ID NO 14
<211> LENGTH: 1575
<212> TYPE: DNA
<213> ORGANISM: Artificial Sequence
<220> FEATURE:
<223> OTHER INFORMATION: DQ401190_JAP_or_US

<400> SEQUENCE: 14
atggaatgga atactttttt cttggtgatc ttgatcatca tcataaagag caccacacca 60
cagatcactc aacgacctcc ggtcgaaaac atctcgacgt accatgcaga ttgggacact 120
ccgctataca ctcatccctc taactgcagg gaagattcct ttgtcccgat tcgaccagct 180
caactcaggt gtcctcatga atttgaagac ataaacaagg gactggtttc cgtcccaact 240
cggatcatcc atctcccgct atcagtcacc agcgtctccg cagtggcgag tggccactac 300
ctgcacagag tgacttatcg agtcacctgt tcgaccagct tctttggagg gcaaaccatc 360
gagaagacaa tcttggaggc gaaattgtct cgtcaggagg ccacaaacga ggcaagcaag 420
gatcacgagt acccgttctt ccccgaaccc tcctgcatct ggatgaaaaa caatgtccat 480
aaggacataa ctcactatta caagacccca aaaacagtat cggtggatct ctacagcagg 540
aaatttctca accctgattt catagagggg gtttgcacaa cctcgccctg tcaaactcat 600
tggcagggag tctattgggt cggtgccaca cctacagccc attgccccac gtcggaaaca 660
ctagaaggac acctgttcac caggacccat gatcacaggg tggtcaaggc aattgtggca 720
ggccatcatc cctggggact cacaatggca tgcacagtga cattttgcgg gacagaatgg 780
atcaagaccg acctgggga cctgatccag gttacaggac cggggggcgc gaggaaactg 840
actccaaaaa agtgtgtcaa taccgatatc cagatgaggg gggcaacaga cgacttttct 900
tatctcaacc atctcatcac caacatggct caaagaaccg agtgcctaga tgcccatagt 960
gatatcaccg cttctgggaa aatctcctca tttctcctct caaagtttcg tccccgccac 1020
cctggacccg gcaaggcaca ctatcttctc gacggtcaaa tcatgcgagg tgactgtgac 1080
tatgaggcag tagtcagcat caactacaat agcgctcaat acaagacggt gaacaacaca 1140
tggaaatcat ggaaacgggt aaacaacaac acagacgggt acgatgggat gatatttggg 1200
gacaaattga tcatcccgga catcgaaaag tatcagagtg tctatgacag tggaatgctc 1260
gttcaaagaa accttgtgga agtccctcat ctgagcattg tgtttgtctc caacacatct 1320
gatctttcca ctaatcacat ccacactaac ctaatccctt cggattggtc attcaactgg 1380
agtctttggc catcattatc tgggatgggg gttgtgggag gggccttcct tctactggta 1440
ctctgctgtt gctgcaaggc atcccctcct attccgaatt acgggattcc gatgcagcag 1500
ttctccagaa gtcagatggt ctgagcacac ctgtccgaat gaccacaatt cttctcttag 1560
gcagatagaa aaaaa 1575

<210> SEQ ID NO 15
<211> LENGTH: 1524
<212> TYPE: DNA
<213> ORGANISM: Artificial Sequence
<220> FEATURE:
<223> OTHER INFORMATION: FJ460590_NorthSea

<400> SEQUENCE: 15
atggaatgga atactttttt cttggtgatc ttgatcatca tcataaagag caccacacca 60
cagatcactc aacgacctcc ggtcgaaaac atctcgacgt accatgcaga ttgggacact 120
ccgctataca ctcatccctc taactgcagg gaagattcct ttgtcccgat tcgaccagct 180
caactcaggt gtcctcatga atttgaagac ataaacaagg gactggtttc cgtcccaact 240
cggatcatcc atctcccgct atcagtcacc agcgtctccg cagtggcgag tggccactac 300
ctgcacagag tgacttatcg agtcacctgt tcgaccggct tctttggagg gcaaaccatc 360
gagaagacaa tcttggaggc gaaattgtct cgtcaggagg ccacaaacga ggcaagcaag 420
gatcacgagt acccgttctt ccccgaaccc tcctgcatct ggatgaaaaa caatgtccat 480
aaggacataa ctcactatta caagacccca aaaacagtat cggtggatct ctacagcagg 540
aaatttctca accctgattt catagagggg gtttgcacaa cctcgccctg tcaaactcat 600
tggcagggag tctattgggt cggtgccaca cctacagccc attgccccac gtcggaaaca 660
ctagaaggac acctgttcac caggaccaat gatcacaggg tggtcaaggc aattgtggca 720
ggccatcatc cctggggact cacaatggca tgcacagtga cattttgcgg gacagaatgg 780
atcaagaccg acctgggggga cctgatccag gttacaggac cgggggggcgc gaggaaactg 840
actccaaaaa agtgtgtcaa taccgatatc cagatgaggg gggcaacaga cgacttttct 900
tatctcaacc atctcatcac caacatggct caaagaaccg agtgcctaga tgcccatagt 960
gatatcaccg cttctgggaa aatctcctca tttctcctct caaagtttcg tcccagccac 1020
cctggacccg gcaaggcaca ctatcttctc gacggtcaaa tcatgcgagg tgactgtgac 1080
tatgaggcag tagtcagcat caactacaat agcgctcaat acaagacggt gaacaacaca 1140
tggaaatcat ggaaacgggt aaacaacaac acagacgggt acgatgggat gatatttggg 1200
gacaaattga tcatcccgga catcgaaaag tatcagagtg tctatgacag tggaatgctc 1260
gttcaaagaa accttgtgga agtccctcac ctgagcattg tgtttgtctc caacacatct 1320
gatctttcca ctaatcacat ccacactaac ctaatccctt cggattggtc attcaactgg 1380
agtctttggc catcattatc tgggatgggg gttgtgggag gggccttcct tctactggta 1440
ctctgctgtt gctgcaaggc atcccctcct attccgaatt acgggattcc gatgcagcag 1500
ttctccagaa gtcagatggt ctga 1524

<210> SEQ ID NO 16
<211> LENGTH: 1967
<212> TYPE: DNA
<213> ORGANISM: Artificial Sequence
<220> FEATURE:
<223> OTHER INFORMATION: AM086382_Fin

<400> SEQUENCE: 16
atggaatgga atactttttt cttggtgatc ttgatcatca tcataaagag caccacacca 60
cagatcactc aacgacctcc ggtcgaaaac atctcgacgt accatgcaga ttgggacact 120
ccgctataca ctcatccctc caactgcagg gaagattcct ttgtcccgat tcgaccagct 180
caactcaggt gtcctcatga atttgaagac ataaacaagg gactggtttc cgtcccaact 240
cagatcatcc atctcccgct atcagtcacc agcgtctccg cagtagcgag tggccactac 300
ctacacagag tgacttatcg agtcacctgt tcgaccagct tctttggagg gcaaaccatc 360
gaaaagacca tcttggaggc gaaattgtct cgtcaggagg ccacaaacga ggcaagtaag 420
gatcacgagt acccgttctt ccctgaaccc tcctgcatct ggatgaagaa caatgtccat 480

```
aaggacataa ctcactatta caagacccca aaaacagtat cggtggatct ctacagcagg    540

aaatttctca accctgattt catagagggg gtctgcacaa cctcgccctg tcaaactcat    600

tggcagggag tctattgggt cggtgccaca cctacagccc attgccccac gtcggaaaca    660

ctagaaggac acctgttcac caggacccat gatcacaggg tggtcaaggc aattgtggca    720

ggccatcatc cctggggact cacaatggca tgcacagtga cattctgcgg gacagaatgg    780

atcaagaccg acctgggga cctgatccag gtgacaggac cgggggcgc gaggaaactg    840

actccaaaaa agtgtgtcaa tgccgatgtc cagatgaggg gggcaacaga cgacttttct    900

tatctcaacc atctcatcac caacatggct caaagaaccg agtgcctaga tgcccatagt    960

gatatcaccg cttctggaaa aatatcctca tttctcctct caaagtttcg tcccagccac   1020

cctggacccg gcaaggcaca ctatcttctc gacggtcaaa tcatgcgagg tgactgtgac   1080

tatgaggcag tagtcagcat caactacaat agcgctcaat acaagacggt gaacaacaca   1140

tggaaatcat ggaaacgggt agacaacaac acagacgggt acgatgggat gatatttggg   1200

gacaaattga tcatcccgga catcgagaag tatcagagtg tctatgacag tggaatgctc   1260

gttcaaagaa accttgtgga agtccctcat ctgagcattg tgtttgtctc caacacatct   1320

gatctttcca ctaatcacat ccacaccaac ctaatccctt cggattggtc attcaactgg   1380

agtctttggc catcattatc tgggatgggg gttgtgggag gggccctcct tctactggta   1440

ctctgctgtt gctgcaaggc gtcccctcct attccaaatt acgggattcc gatgcagcag   1500

ttctccagaa gtcagacggt ctgagcacac ctgtccggat gaccacaatt cctctcttag   1560

gtagatagaa aaaaatggca cctttgtgat aaagaaacat ggcgacccaa cccgcgctca   1620

gcacaaccag cttctctccg ctcgtcctcc gcgagatgat cacacacaga ctcaaatttg   1680

acccaagcaa ctacctcaac tgtgaccttg atcggtcgga catatccacc atggacttct   1740

ttgaaacgac cctccccagg atcctagatg atctgagggc cagtacacgg cttccctacc   1800

tccatgtgct cgacatgagg ataagtctcc tagagagaac ccactacatg ttcagaaacg   1860

tcccctctag tcccgccaca accggtaggc tgacagatcc tggactcatc attatttcac   1920

atgcggaggt ggggatattg acaagtggct ctgggctcac ctcctga                1967
```

<210> SEQ ID NO 17
<211> LENGTH: 1524
<212> TYPE: DNA
<213> ORGANISM: Artificial Sequence
<220> FEATURE:
<223> OTHER INFORMATION: AY546577_Baltic

<400> SEQUENCE: 17

```
atggaatgga atacttttt cttagtgatt ttgatcatca tcataaaaag caccacgtca     60

cagatcactc aacgacctcc ggccgagaac atctcaactt accatgcaga ttgggacact    120

ccactataca ctcatccctc caactgcagg gaagattcct ttgtccctat tcgaccagct    180

caactaaggt gtcctcatga atttgaagac ataaacaagg gattggtatc cgtccctact    240

cagattgttc atctcccgtt atcagtcact agcgtctccg cagttgcaag tggtcactac    300

ctgcacagag tgacctatcg agtcacctgc tcaaccagct tctttggagg gcaaaccatc    360

gaaaagacca tcctggaagc gaagctgtct cgtcaagagg ccatagatga ggcaagcaaa    420

gatcatgagt acccgttctt tcctgaacct tcctgcattt ggatgaagaa caatgttcac    480

aaggacataa ctcactatta caagacccca agaacagtat ctgtcgacct ctatagcagg    540
```

```
aaatttctca accctgattt catagagggg gtttgtacga cctcgccttg tcagactcat    600

tggcagggag tctattgggt cggtgccaca cccacggctc attgtcccgt gtcagaaacg    660

ctagaaggac acctgttcac cagaacccat gatcataggg tggtcaaggc aatcgtggca    720

ggccatcacc cctggggact cacaatggca tgcacagtga cattctgtgg gacggagtgg    780

atcaagaccg acctggggga cctgatcaag gtgacagtgc aggggggtga gcagaaactg    840

actccggaaa agtgtattaa caccgacgtt cagatgaggg ggcaacgga cgacttctcc     900

tatctcggcc atctcatcac taatatggct caaagaactg agtgcctaga tgctcacagt    960

gacatcactg cctctgggaa gatatcttct tttctcctat caaagttccg tcccaatcac   1020

cctggacccg gtaaggcaca ctatcttctt gatggtcaga tcatgcgagg tgactgtgac   1080

tatgaggcgg tagtcagcat caactacaac agcgctcaat acaagacggt gaacaacacc   1140

tggaaatcat ggaagcggat aggcaacaac acagatgggt acgatgggat gatatttggg   1200

gacaagctgg taatcccaga catcgagaaa tatcagagca tctatgacag tggaatgctc   1260

gttcaaagaa acctggcaga agttcctcat ctgagcgttg tgtttgtctc caacacatcc   1320

gatctttcca ccaattacat ccacaccaat ctgatccctt cagattggtc cttcaactgg   1380

agcctttggc cgtcgttatt tggratggga gtcgtgggag tgatcctcct tctgctgata   1440

ttctgttgtt gctgcaaagc gtcccctccc attccaaact atgggattcc tatgcagcaa   1500

ttctccagaa accagatgat ctga                                          1524
```

<210> SEQ ID NO 18
<211> LENGTH: 1524
<212> TYPE: DNA
<213> ORGANISM: Artificial Sequence
<220> FEATURE:
<223> OTHER INFORMATION: AY546578_Baltic

<400> SEQUENCE: 18

```
atggaatgga atactttttt cttagtgatt ttgatcatca tcataaaaag caccacgtca     60

cagatcactc aacgacctcc ggccgagaac atctcaactt accatgcaga ttgggacact    120

ccactataca ctcatccctc caactgcagg gaagattcct ttgtccctat tcgaccagct    180

caactaaggt gtcctcatga atttgaagac ataaacaagg gattggtatc cgtccctact    240

cagattgttc atctcccgtt atcagtcact agcgtctccg cagttgcaag tggtcactac    300

ctgcacagag tgacctatcg agtcacctgc tcaaccagct tctttggagg gcaaaccatc    360

gaaaagacca tcctggaagc gaagctgtct cgtcaagagg ccatagatga ggcaagcaaa    420

gatcatgagt acccgttctt tcctgaacct tcctgcattt ggatgaagaa caatgttcac    480

aaggacataa ctcactatta caagacccca agaacagtat ctgtcgacct ctatagcagg    540

aaatttctca accctgattt catagagggg gtttgtacga cctcgccttg tcagactcat    600

tggcagggag tctattgggt cggtgccaca cccacggctc attgtcccgt gtcagaaacg    660

ctagaaggac acctgttcac cagaacccat gatcataggg tggtcaaggc aatcgtggca    720

ggccatcacc cctggggact cacaatggca tgcacagtga cattctgtgg gacggagtgg    780

atcaagaccg acctggggga cctgatcaag gtgacagtgc aggggggtga gcagaaactg    840

actccggaaa agtgtattaa caccgacgtt cagatgaggg ggcaacgga cgacttctcc     900

tatctcggcc atctcatcac taatatggct caaagaactg agtgcctaga tgctcacagt    960

gacatcactg cctctgggaa gatatcttct tttctcctat caaagttccg tcccaatcac   1020

cctggacccg gtaaggcaca ctatcttctt gatggtcaga tcatgcgagg tgactgtgac   1080
```

```
tatgaggcgg tagtcagcat caactacaac agcgctcaat acaagacggt gaacaacacc   1140

tggaaatcat ggaagcggat aggcaacaac acagatgggt acgatgggat gatatttggg   1200

gacaagctgg taatcccaga catcgagaaa tatcagagca tctatgacag tggaatgctc   1260

gttcaaagaa acctggcaga agttcctcat ctgagcgttg tgtttgtctc caacacatcc   1320

gatctttcca ccaattacat ccacaccaat ctgatccctt cagattggtc cttcaactgg   1380

agcctttggc cgtcgttatc tgggatggga gtcgtgggag tgatcctcct tctgctgata   1440

ttctgttgtt gctgcaaagc gtcccctccc attccaaact atgggattcc tatgcagcaa   1500

ttctccagaa accagatgat ctga                                          1524

<210> SEQ ID NO 19
<211> LENGTH: 1524
<212> TYPE: DNA
<213> ORGANISM: Artificial Sequence
<220> FEATURE:
<223> OTHER INFORMATION: AY546620_Ire

<400> SEQUENCE: 19

atggaatgga atactttttt cttggtgatc ttgatcattc tcgtaaagag caccacatca     60

cagatcaccc aaagacctcc ggtcgagaac atctcgacgt accatgaaga ttgggacact    120

ccgttgtaca ctcacccctc caactgcaga gaggactcct ttgtcccgat tcgaccagct    180

caactcaggt gtcctcatga atttgaagac atcaacaagg gactggtctc cgttccaact    240

cagatcattc atctcccgct atcagtcacc agcgtctccg cagttgcaag tggccactac    300

ctgcacagag tgacctatcg agtcacctgc tcaaccagct tctttggggg acaaaccatc    360

gaaaagacca tcctggaagc aaaattgtct cgtcaggagg ccgcaaatga ggcaagcaaa    420

gaccatgagt acccgttctt tcctgaaccc tcctgcatct ggatgaaaaa taatgtccat    480

aaggatataa ctcactatta taagacccca aaaacagtct ctgtggatct ctacagcagg    540

aaatttctta accctgattt catagagggg gtttgtacga cctcgccctg tcagactcat    600

tggcagggag tctattgggt cggtgccaca cccacagccc attgtcccac ttcagaaaca    660

ctagaggggc acctgttcac cagaactcat gatcacagag tggtcaaggc aattgtggcg    720

ggccatcacc catggggact cacgatggca tgcacagtga cattctgtgg gacagattgg    780

atcaagaccg acctggggga cctgatcaag gtggtaggac agggaggcga aaaaaacctg    840

actccaaaaa aatgtgtcaa tactgacatc cagatgaggg gggcaacaga cgacttctcc    900

tatctcaacc atctcatcac aaacatggct caaaggaccg agtgtctaga cgcccatagt    960

gacatcactg cctccgggaa aatatcctcg tttctcctct caaagtttcg tcccagccac   1020

cccggacccg gcaaggcaca ttacctccgt gatggtctga tcatgcgagg tgactgtgac   1080

tatgaggcgg tagtcagtat caactacaat agcgctcagt acaagacggt gaacaacaca   1140

tggaagtcat ggaaacggat agacaacaat acagatgggt acgatgggat gatatttgga   1200

gacaaactga tcatcccaga catcgagaaa tatcagagta tctacgatag tgggatgctc   1260

gttcaaagga acctggtgga agttcctcat ctgagcattg tgtttgtctc caacacatct   1320

gatctctcca ccaatcacat ccacaccaac ttaatcccct cggattggtc attcaactgg   1380

agcctctggc cgtcattatc agggatggga gttgtgggag ggccttcct tctattggta   1440

ctttgctgtt gttgcaaagc gtctcctcct attccaaatt acgggattcc tatgcagcaa   1500

ttctccagaa atcagatggt ctga                                          1524
```

<210> SEQ ID NO 20
<211> LENGTH: 1524
<212> TYPE: DNA
<213> ORGANISM: Artificial Sequence
<220> FEATURE:
<223> OTHER INFORMATION: AY546618_France

<400> SEQUENCE: 20
atggaatgga atactttttt cttggtgatc ttgatcatta tcataaagag caccacatca 60
cagatcaccc aaagacctcc ggtcgagaac atctcgacgt accatgcaga ttgggacact 120
cctttataca ctcacccctc caactgcaga gaagactcct ttgtcccgat tcgaccagct 180
caactcaggt gtcctcatga atttgaagac atcaacaagg gactagtctc cgttcccact 240
cagatcattc atctcccgct atcagtcacc agcgtctccg cagttgcaag tggccactac 300
ttgcacagag tgacctatcg agtcacctgc tcaaccagct tctttggggg acaaaccatc 360
gaaaagacca tcctggaagc aaaattgtct cgtcaggagg ccgtaaatga ggcaagcaaa 420
gaccatgagt acccgttctt tcctgaaccc tcctgcatct ggatgaaaaa taatgtccat 480
aaagatataa ctcactatta taagacccca aaaacagtct ctgtggatct ctacagcagg 540
aaatttctta accctgattt catagagggg gtttgtacga cctcgccctg tcagactcat 600
tggcagggag tctattgggt cggtgccaca cctacagccc attgtcccac ttcagaaaca 660
ctagaggggc acctgttcac cagaactcat gatcacaggg tggtcaaggc aattgtggcg 720
ggccaccacc catggggact cacgatggca tgcacagtga cattctgtgg aacagattgg 780
atcaagaccg acctggggga cctgatcaag gtgataggac agggggcga aaaaaaactg 840 actccaaaaa aatgtgtcaa taccgacatc cagatgaggg gggcaacaga cgacttctcc 900
tatctcaacc atctcatcac aaacatggct ccaaggaccg agtgtctaga cgcccatagt 960
gacatcactg cctccgggaa aatatcctcg tttctcctct caaagtttcg tcccagccac 1020
cccggacccg gcaaggcaca ttacctcctt gatggtcaaa tcatgcgagg tgactgtgac 1080
tatgaggcgg tagtaagtat caactacaat agcgctcagt acaagacggt gaacaacaca 1140
tggaagtcat ggaaacggat aggcaacaat acagatgggt acgatgggat gatatttgga 1200
gacaaactgg tcatcccaga catcgagaaa tatcagagta tctatgatag tgggatgctt 1260
gttcaaagga acctggtgga agttcctcat ctgagcattg tgtttgtctc caacacatct 1320
gatctctcca ccaatcacat ccacaccaac ttaatcccct cggattggtc attccactgg 1380
agcctctggc cgtcattatc agggatggga attgtgggag gggccttcct tctattggta 1440
ctttgctgtt gctgcaaagc gtctcctcct attccaaatt acgggattcc tatgcagcaa 1500
ttctccagaa atcagatggt ctga 1524

<210> SEQ ID NO 21
<211> LENGTH: 1524
<212> TYPE: DNA
<213> ORGANISM: Artificial Sequence
<220> FEATURE:
<223> OTHER INFORMATION: VHSV_KOR_FYeosu05

<400> SEQUENCE: 21
atggaatgga atactttttt cttggtgatt ctggtcatca tcataaaaag caccacatca 60
cagatcactc aacgacctcc ggtcgagaac atctcaacat accatgtaga ctgggacact 120
ccactgtata ctcacccctc caactgcaga aaaaactcct ttgttccgat tcggccagat 180
caactcaggt gtccccatga gttcgaggac acaaacaagg gcttggtctc tgtcccagcc 240

```
cagatcatcc atcttccgtt atcagtcacc agcgtctcag cagtcgcaaa tggccactac    300
ctacacagag tgacctaccg ggtcacctgc tcaaccaatt tctttggagg acaaaccatt    360
gaaaaaacca tcctggaggc aaagctgtcc cgtcaagagg ccatcaatga ggctggcaag    420
gatcacgagt accctttctt ccccgaacct tcctgcatct ggatgaagga caatgtccac    480
aaggacataa ctcactatta caagacccca aagacagtgt ccattgacct ctacagtaga    540
aagtttctaa accctgactt catagagggg gtttgtacaa catcaccctg cccaacccac    600
tggcaaggag tctactggat cggcgctaca cctcaggccc attgccctac ctcagaaacg    660
cttaaggggc atctgttcac caggacacat gatcacaggg tggtcaaggc aatcgttgcg    720
ggtcaccacc cctgggggct cacaatggca tgcaaggtga cattttgtgg gacagaatgg    780
atcaagaccg acctggggga ccttattcag gtgacagggc aggggggagc gaataaactg    840
tctccaaaga agtgtgtcaa caccgacgtt cagatgaggg gagccacaga cgacttctct    900
tatcttaacc atctcattac caacatggct caaagaactg agtgcctgga tgcccacagt    960
gatatcactg cctctgggaa gatatcccct tttctcctct caaagtttcg tcctagtcac   1020
ccggggccgg gcaaggcaca ttatttcctt gatggccaga tcatgcgagg tgagtgtgat   1080
tacgaggccg tggtcagcat caactacaac agtgctcagt acaagacggt aaacaacatc   1140
tggaaatcat ggaatcggat agacaacaac actgacgggt atgatggaat gatattcggg   1200
gacaaattga tcatcccaga tatcgagaaa taccagagca tctatgacag cggaatgctt   1260
gttcaaagaa acctggtgga aattccccat ccgagcattg tgttcgtctc caacacatct   1320
gatctctcca ctaactacat ccacaccaat ctaattcctt cggattggtc attcaattgg   1380
agtctttggc cgtcactatc aggaatgggg gtagtgggag gggccttcct tctgctcgtg   1440
ctctgctgtt gctgcagggc atctccccct cctccgagtt acgggattcc gatgcagcag   1500
ttctccagaa gccagatggt ctga                                          1524
```

<210> SEQ ID NO 22
<211> LENGTH: 1521
<212> TYPE: DNA
<213> ORGANISM: Artificial Sequence
<220> FEATURE:
<223> OTHER INFORMATION: VHSV2005_01_KORJeju

<400> SEQUENCE: 22

```
atggaatgga atacttttc cttggtgatt ctggtcatca tcataaaaag caccacatca      60
cagatcactc aacgacctcc ggtcgagaac atctcaacat accatgtaga ctgggacact    120
ccactgtata ctcacccctc caactgcaga aaaaactcct ttgttccgat tcggccagat    180
caactcaggt gtccccatga gttcgaggac acaaacaagg gcttggtctc tgtcccagcc    240
cagatcatcc atcttccgtt atcagtcacc agcgtctcag cagtcgcaaa tggccactac    300
ctacacagag tgacctaccg ggtcacctgc tcaaccaatt tctttggagg acaaaccatt    360
gaaaaaacca tcctggaggc aaagctgtcc cgtcaagagg ccatcaatga ggctggcaag    420
gatcacgagt accctttctt ccccgaacct tcctgcatct ggatgaagga caatgtccac    480
aaggacataa cccactatta caagacccca aagacagtgt ccattgacct ctacagtaga    540
aagtttctaa accctgactt catagagggg gtttgtacaa catcaccctg cccaacccac    600
tggcaaggag tctactggat cggcgctaca cctcaggccc attgccctac ctcagaaacg    660
cttaaggggc gtctgttcac caggacacat gatcacaggg tggtcaaggc aatcgttgcg    720
```

-continued

```
ggtcaccacc cctgggggct cacaatggca tgcaaggtga cattttgtgg gacagaatgg     780

atcaagaccg acctggggga ccttattcag gtgacagggc aggggggagc gaataaactg     840

tctccaaaga agtgtgtcaa caccgacgtt cagatgaggg gagccacaga cgacttctct     900

tatcttaacc atctcattac caacatggct caaagaactg agtgcctgga tgcccacagt     960

gatatcactg cctctgggaa gatatcccct tttctcctct caaagtttcg tcctagtcac    1020

ccggggccgg gcaaggcaca ttatctcctt gatggccaga tcatgcgagg tgagtgtgat    1080

tatgaggccg tggtcagcat caactacaac agtgctcagt acaagacggt aaacaacatc    1140

tggaaatcat ggaatcggat agacaacaac actgacgggt atgatggaat gatatccggg    1200

gacaaattga tcatcccaga tatcgagaaa taccagagca tctatgacag cggaatgctt    1260

gttcaaagaa acctggtgga aattccccat ccgagcattg tgttcgtctc caacacatct    1320

gatctctcca ctaactacat ccacaccaat ctaattcctt cggattggtc attcaattgg    1380

agtctttggc cgtcactatc aggaatgggg gtagtgggag gggccttcct tctgctcgtg    1440

ctctgctgtt gctgcagggc atctcccccct cctccgagtt acgggattcc gatgcagcag    1500

ttctccagaa gtcagacggt c                                              1521
```

<210> SEQ ID NO 23
<211> LENGTH: 1521
<212> TYPE: DNA
<213> ORGANISM: Artificial Sequence
<220> FEATURE:
<223> OTHER INFORMATION: VHSV2010_01_KORGeoJe

<400> SEQUENCE: 23

```
atggaatgga atactttttc cttggtgatt ctggtcatca tcataaaaag caccacatca      60

cagatcactc aacgacctcc ggtcgagaac atctcaacat accatgtaga ctgggacact     120

ccactgtata ctcacccctc caactgcaga aaaaactcct ttgttccgat tcggccagat     180

caactcaggt gtccccatga gttcgaggac acaaacaagg gcctggtctc tgtcccagcc     240

cagatcatcc atcttccgtt atcagttacc agcgtctcag cagtcgcaaa tggccactac     300

ctacacagag tgacctaccg ggtcacctgc tcaaccaatt tctttggagg acaaaccatt     360

gaaaaaacca tcctggaggc aaagctgtcc cgtcaagagg ccatcaatga ggctggcaag     420

gatcacgagt accctttctt ccccgaacct tcctgcatct ggataaagga caatgtccac     480

aaggacataa cccactatta caagacccca aagacagtgt ccattgacct ctacagtaga     540

aagtttctaa accctgactt catagagggg gtttgtacaa catcaccctg cccaacccac     600

tggcaaggag tctactggat cggcgctaca cctcaggccc attgccctac ctcagaaacg     660

cttcaggggc atctgttcac caggacacat gatcacaggg tggtcaaggc aatcgttgcg     720

ggtcaccacc cctgggggct cacaatggca tgcaaggtga cattttgtgg gacagaatgg     780

atcaagaccg acctggggga ccttattcag gtgacagggc aggggggagc gaataaactg     840

tctccaaaga agtgtgtcaa caccgacgtt cagatgaggg gagccacaga cgacttctct     900

tatcttaacc atctcattac caacatggct caaagaactg agtgcctgga tgcccacagt     960

gatatcactg cctctgggaa gatatcccct tttctcctct caaagtttcg tcctagtcac    1020

ccggggccgg gcaaggcaca ttatctcctt gatggccaga tcatgcgagg tgagtgtgat    1080

tacgaggccg tggtcagcat caactacaac agtgctcagt acaagacggt aaacaacatc    1140

tggaaatcat ggaatcggat agacaacaac actgacgggt atgatggaat gatattcggg    1200

gacaaattga tcatcccaga tatcgagaaa taccagagca tctatgacag cggaatgctt    1260
```

gttcaaagaa acctggtggg aattccccat ccgagcattg tgttcgtctc caacacatct 1320
gatctctcca ctaactacat ccacaccaat ctaattcctt cggattggtc attcaattgg 1380
agtctttggc cgtcactatc aggaatgggg gtagtgggag gggccttcct tctgcttgtg 1440
ctctgttgtt gctgcagggc atctcccccct cctccgagtt acgggattcc gatgcagcag 1500
ttctccagaa gtcagacggt c 1521

<210> SEQ ID NO 24
<211> LENGTH: 1521
<212> TYPE: DNA
<213> ORGANISM: Artificial Sequence
<220> FEATURE:
<223> OTHER INFORMATION: VHSV2010_02_KORPohang

<400> SEQUENCE: 24
atggaatgga atactttttc cttggtgatt ctgatcatca tcataaaaag caccacatca 60
cagatcactc aacgacctcc ggtcgagaac atctcaacat accatgtaga ctgggacact 120
ccactgtata ctcacccctc caactgcaga aaaaactcct ttgttccgat tcggccagat 180
caactcaggt gtccccatga gttcgaggac acaaacaagg gcttggtctc tgtcccagcc 240
cagatcatcc atcttccgtt atcagtcacc agcgtctcag cagtcgcaaa tggccactac 300
ctacacagag tgacctaccg ggtcacctgc tcaaccaatt tctttggagg acaaaccatt 360
gaaaaaacca tcctggaggc aaagctgtcc cgtcaagagg ccatcaatga ggctggcaag 420
gatcacgagt accctttctt ccccgaacct tcctgcatct ggatgaagga caatgtccac 480
aaggacataa cccactatta caagacccca aagacagtgt ccattgacct ctacagtaga 540
aagtttctaa accctgactt catagagggg gtttgtacaa catcaccccg cccaacccac 600
tggcaaggag tctactggat cggcgctaca cctcaggccc actgcccgac ctcagaaacg 660
cttaaggggc atctgttcac caggacacat gatcacaggg tggtcaaggc aatcgttgcg 720
ggtcaccacc cctggggact cacaatggca tgcaaggtga cattttgtgg gacagaatgg 780
atcaagaccg acctggggga ccttattcag gtgacagggc agggggagc gaataaactg 840 tctccaaaga ggtgtgtcaa caccgacgtt cagatgaggg gagccacaga cgacttctct 900
tatcttaacc atctcattac caacatggct caaagaactg agtgcctgga cgcccacagt 960
gatatcactg cctctgggaa gatatcccct tttctcctct caaagtttcg tcctagtcac 1020
ccggggccgg gcaaggcaca ttatctcctt gatggccaga tcatgcgagg tgagtgtgat 1080
tacgaggccg tggtcagcat caactacaac agtgctcagt acaagacggt aaacaacacc 1140
tggaaaccat ggaatcggat agacaacaac actgacgggt atgatggaat gatattcggg 1200
gacaaattga tcatcccaga catcgagaaa taccagagca tctatgacag cggaatgctt 1260
gttcaaagaa acctggtgga aattccccat ccgagcattg tgttcgtctc caacacatct 1320
gatctctcca ctaactacat ccacaccaat ctaattcctt cggattggtc attcaattgg 1380
agtctttggc cgtcactatc aggaatgggg gtagtgggag gggccttcct tctgctcgtg 1440
ctctgctgtt gctgcagggc atctcccccct cctccgagtt acgggattcc aatgcagcag 1500
ttctccagaa gtcagacggt c 1521

<210> SEQ ID NO 25
<211> LENGTH: 1521
<212> TYPE: DNA
<213> ORGANISM: Artificial Sequence
<220> FEATURE:

<223> OTHER INFORMATION: VHSV2011_01_KORJeju

<400> SEQUENCE: 25
atggaatgga atactttttc cttggtgatt ctggtcatca tcataaaaag caccacatca 60
cagatcactc aacgacctcc ggtcgagaac atctcaacat accatgtaga ctgggacact 120
ccactgtata ctcacccctc caactgcaga aaaaactcct ttgttccgat tcggccagat 180
caactcaggt gtccccatga gttcgaggac ataaacaagg gcttggtctc tgtcccagcc 240
cagatcatcc atcttccgtt atcagtcacc agcgtctcag cagtcgcaaa tggccactac 300
ctacacaggg tgacctaccg ggtcacctgc tcaaccaatt tctttggagg acaaaccatt 360
gaaaaaacca tcctggaggc aaagctgtcc cgtcaagagg ccatcaatga ggctggcaag 420
gatcacgagt accctttctt ccccgaacct tcctgcatct ggatgaagga caatgtccac 480
aaggacataa cccactatta caagacccca aaaacagtgt ccattgacca ctacagtaga 540
aagtttctaa accctgactt catagagggg gtttgtacaa catcaccctg cccaacccac 600
tggcaaggag tctactggat cggcgctaca cctcaggccc attgccctac ctcagaaaca 660
cttaaggggc atctgttcac caggacacat gatcacaggg tggtcaaggc aatcgttgcg 720
ggtcaccacc cctgggggct cacaatggca tgcaaggtga cattttgtgg gacagaatgg 780
atcaagaccg acctggggga ccttattcag gtgacagggc agggggagc gaataaactg 840 tctccaaaga agtgtgtcaa caccgacgtt cagatgaggg gagccacaga cgacttctct 900
tatcttaacc atcttatcac caacatggct caaagaactg agtgcctgga tgcccacagt 960
gatatcactg cctctgggaa gatatcccct tttctcctct caaagtttcg tcctagtcac 1020
ccggggccgg gcacggcaca ttatctcctt gatggccaga tcatgcgagg tgagtgtgat 1080
tacgaggccg tggtcagcat caactacaac agtgctcagt acaagacggt aaacaacatc 1140
tggaaatcat ggaatcggat agacaacaac actgacgggt atgatggaat gatattcggg 1200
gacaaattga tcatcccaga tatcgagaaa taccagagca tctatgacag cggaatgctt 1260
gttcaaagaa acctggtgga aattccccat ccgagcattg tgttcgtctc caacacatct 1320
gatctctcca ctaactacat ccacaccaat ctaattcctt cggattggtc attcaattgg 1380
agtctttggc cgtcactatc aggaatgggg gtagtgggag gggccttcct tctgcttgtg 1440
ctctgctgtt gctgcagggc atctccccct cctccgagtt acgggattcc gatgcagcag 1500
ttctccagaa gtcagacggt c 1521

<210> SEQ ID NO 26
<211> LENGTH: 1524
<212> TYPE: DNA
<213> ORGANISM: Artificial Sequence
<220> FEATURE:
<223> OTHER INFORMATION: VHSV_IVaKRYGHWando

<400> SEQUENCE: 26
atggaatgga atactttttt cttggtgatt ctggtcatca tcataaaaag caccacatca 60
cagatcactc aacgacctcc ggtcgagaac atctcaacat accatgtaga ctgggacact 120
ccactgtata ctcacccctc caactgcaga aaaaactcct ttgttccgat tcggccagat 180
caactcaggt gtccccatga gttcgaggac acaaacaagg gcttggtctc tgtcccagcc 240
cagatcatcc atcttccgtt atcagtcacc agcgtctcag cagtcgcaaa tggccactac 300
ctacacagag tgacctaccg ggtcacctgc tcaaccaatt tcttcggagg acaaaccatt 360
gaaaaaacca tcctggaggc aaagctgtcc cgtcaagagg ccatcaatga ggctggcaag 420

```
gatcacgagt accctttctt ccccgaacct tcctgcatct ggatgaagga caatgtccac    480

aaggacataa cccactatta caagacccca aagacagtgt ccattgacct ctacagtaga    540

aagtttctaa accctgactt catagagggg gtttgtacaa catcaccctg cccaacccac    600

tggcaaggag tctactggat cggcgctaca cctcaggccc attgccctac ctcggaaacg    660

cttaaggggc atctgttcac caggacacat gatcacaggg tggtcaaggc aatcgttgcg    720

ggtcaccacc cctgggggct cacaatggca tgcaaggtga cattttgtgg gacagaatgg    780

atcaagaccg acctggggga ccttattcag gtgacagggc agggggagc gaataaactg    840

tctccaaaga agtgtgtcaa caccgacgtt cagatgaggg gagccacaga cgacttctct    900

tatcttaacc atctcattac caacatggct caaagaactg agtgcctgga tgcccacagt    960

gatatcactg cctctgggaa gatatcccct tttctcctct caaagtttcg tcctagtcac   1020

ccggggccgg gcaaggcaca ttatctcctt gatggccaga tcatgcgagg tgagtgtgat   1080

tacgaggccg tggtcagcat caactacaac agtgctcagt acaagacggt aaacaacatc   1140

tggaaatcat ggaatcggat agacaacaac actgacgggt atgatggaat gatattcggg   1200

gacaaattga tcatcccaga tatcgagaaa tatcagagca tctatgacag cggaatgctt   1260

gttcaaagaa acctggtgga aattccccat ccgagcattg tgttcgtctc caacacatct   1320

gatctctcca ctaactacat ccacaccaat ctaattcctt cggattggtc attcaattgg   1380

agtctttggc cgtcactatc aggaatgggg gtagtgggag ggccttcct tctgcttgtg   1440

ctctgttgtt gctgcagggc atctcccccct cctccgagtt acgggattcc gatgcagcag   1500

ttctccagaa gtcagacggt ctga                                          1524
```

```
<210> SEQ ID NO 27
<211> LENGTH: 1524
<212> TYPE: DNA
<213> ORGANISM: Artificial Sequence
<220> FEATURE:
<223> OTHER INFORMATION: VHSV_IVaKRCJAJeju

<400> SEQUENCE: 27

atggaatgga atactttttt cttggtgatt ctggtcatca tcataaaaag caccacatca     60

cagatcactc aacgacctcc ggtcgagaac atctcaacat accatgtaga ctgggacact    120

ccactgtata ctcacccctc caactgcaga aaaaactcct ttgttccgat tcggccagat    180

caactcaggt gtccccatga gttcgaggac acaaacaagg gcttggtctc tgtcccagcc    240

cagatcatcc atcttccgtt atcagtcacc agcgtctcag cagtcgcaaa tggccactac    300

ctacacagag tgacctaccg ggtcacctgc tcaaccaatt tcttcggagg acaaaccatt    360

gaaaaaacca tcctggaggc aaagctgtcc cgtcaagagg ccatcaatga ggctggcaag    420

gatcacgagt accctttctt ccccgaacct tcctgcatct ggatgaagga caatgtccac    480

aaggacataa cccactatta caagacccca aagacagtgt ccattgacct ctacagtaga    540

aagtttctaa accctgactt catagagggg gtttgtacaa catcaccctg cccaacccac    600

tggcaaggag tctactggat cggcgctaca cctcaggccc attgccctac ctcggaaacg    660

cttaaggggc atctgttcac caggacacat gatcacaggg tggtcaaggc aatcgttgcg    720

ggtcaccacc cctgggggct cacaatggca tgcaaggtga cattttgtgg gacagaatgg    780

atcaagaccg acctggggga ccttattcag gtgacagggc agggggagc gaataaactg    840

tctccaaaga agtgtgtcaa caccgacgtt cagatgaggg gagccacaga cgacttctct    900
```

-continued

```
tatcttaacc atctcattac caacatggct caaagaactg agtgcctgga tgcccacagt     960

gatatcactg cctctgggaa gatatcccct tttctcctct caaagtttcg tcctagtcac    1020

ccggggccgg gcaaggcaca ttatctcctt gatggccaga tcatgcgagg tgagtgtgat    1080

tacgaggccg tggtcagcat caactacaac agtgctcagt acaagacggt aaacaacatc    1140

tggaaatcat ggaatcggat agacaacaac actgacgggt atgatggaat gatattcggg    1200

gacaaattga tcatcccaga tatcgagaaa tatcagagca tctatgacag cggaatgctt    1260

gttcaaagaa acctggtgga aattccccat ccgagcattg tgttcgtctc caacacatct    1320

gatctctcca ctaactacat ccacaccaat ctaattcctt cggattggtc attcaattgg    1380

agtctttggc cgtcactatc aggaatgggg gtagtgggag gggccttcct tctgcttgtg    1440

ctctgttgtt gctgcagggc atctccccct cctccgagtt acgggattcc gatgcagcag    1500

ttctccagaa gtcagacggt ctga                                           1524
```

<210> SEQ ID NO 28
<211> LENGTH: 1524
<212> TYPE: DNA
<213> ORGANISM: Artificial Sequence
<220> FEATURE:
<223> OTHER INFORMATION: VHSV_strainKJ2008Korea

<400> SEQUENCE: 28

```
atggaatgga atacttttttt cttggtgatt ctggtcatca tcataaaaag caccacatca      60

cagatcactc aacgacctcc ggtcgagaac atctcaacat accatgcaga ctgggacact     120

ccactgtata ctcacccctc caactgcaga aaaaactcct ttgttccgat tcggccagat     180

caactcaggt gtccccatga gttcgaggac acaaacaagg gcttggtctc tgtcccagcc     240

cagatcatcc atcttccgtt atcagtcacc agcgtctcag cagtcgcaaa tggccactac     300

ctacacagag tgacctaccg ggtcacctgc tcaaccaatt tctttggagg acaaaccatt     360

gaaaaaacca tcctggaggc aaagctgtcc cgtcaagagg ccatcaatga ggctggcaag     420

gatcacgagt accctttctt ccccgaacct tcctgcatct ggatgaagga caatgtccac     480

aaggacataa cccactatta caagacccca aagacagtgt ccattgacct ctacagtaga     540

aagtttctaa accctgactt catagagggg gtttgtacaa catcaccctg cccaacccac     600

tggcaaggag tctactggat cggcgctaca cctcaggccc attgccctac ctcagaaacg     660

cttaaggggc atctgttcac caggacacat gatcacaggg tggtcaaggc aatcgttgcg     720

ggtcaccacc cctgggggct cacaatggca tgcaaggtga cattctgtgg gacagaatgg     780

atcaagaccg acctggggga ccttattcag gtgacagggc agggggagc gaataaactg      840

tctccaaaga agtgtgtcaa caccgacgtt cagatgaggg gagccacaga cgacttctct     900

tatcttaacc atctcattac caacatggct caaagaactg agtgcctgga tgcccacagt     960

gatatcactg cctctgggaa gatatcccct tttctcctct caaagtttcg tcctagtcac    1020

ccggggccgg gcaaggcaca ttatctcctt gatggccaga tcatgcgagg tgagtgtgat    1080

tacgaggccg tggtcagcat caactacaac agtgctcagt acaagacggt aaacaacatc    1140

tggaaatcat ggaatcggat agacaacaac actgacgggt atgatggaat gatattcggg    1200

gacaaattga tcatcccaga tgtcgagaaa taccagagca tctatgacag cggaatgctt    1260

gttcaaagaa acctggtgga aattccccat ccgagcattg tgttcgtctc caacacatct    1320

gatctctcca ctaactacat ccacaccaat ctaattcctt cggattggtc attcaattgg    1380

agtctttggc cgtcactatc aggaatgggg gtagtgggag gggccttcct tctgctcgtg    1440
```

```
ctctgctgtt gctgcagggc atctccccct cctccgagtt acgggattcc gatgcagcag   1500

ttctccagaa gccagatggt ctga                                          1524


<210> SEQ ID NO 29
<211> LENGTH: 1524
<212> TYPE: DNA
<213> ORGANISM: Artificial Sequence
<220> FEATURE:
<223> OTHER INFORMATION: VHSV_PORVChina

<400> SEQUENCE: 29

atggaatgga atactttttt cttggtgatt ctgatcatca tcataaaaag caccacatca     60

cagatcactc aacgacctcc ggtcgagaac atctcaacat accatgtaga ctgggacact    120

ccactgtata ctcacccctc caactgcaga aaaaactcct ttgttccgat tcggccagat    180

caactcaggt gtccccatga gttcgaggac acaaacaagg gcttggtctc tgtcccagcc    240

cagatcatcc atcttccgtt atcagtcacc agcgtctcag cagtcgcaaa tggccactac    300

ctacacagag tgacctaccg ggtcacctgc tcaaccaatt tctttggagg acaaaccatt    360

gaaaaaacca tcctggaggc aaagctgtcc cgtcaagagg ccatcaatga ggctggcaag    420

gatcacgagt accctttctt ccccgaacct tcctgcatct ggatgaagga caatgtccac    480

aaggacataa cccactacta caagacccca aagacagtgt ccattgacct ctacagtaga    540

aagtctccaa accctgactt catagagggg gtttgtacaa catcaccctg cccaacccac    600

tggcaaggag tctactggat cggcgctaca cctcaggccc actgcccgac ctcagaaacg    660

cttaaggggc atctgtttac caggacacat gatcacaggg tggtcaaggc aatcgttgcg    720

ggtcaccacc cctggggact cacaatggca tgcacggtga cattttgtgg gacagaatgg    780

atcaagaccg acctggggga cctcattcag gtgacagggc agggggagc gaacaaactg     840

tctccaaaga ggtgtgtcaa caccgacgtt cagatgaggg gagccacaga cgacttctct    900

tatcttaacc atctcattac caacatggct caaagaactg agtgcctgga cgcccacagt    960

gatatcactg cctctgggaa gatatcccct tttctcctct caaagtttcg tcctagtcac   1020

ccggggccgg gcaaggcaca ttatctcctt gatggccaga tcatgcgagg tgagtgtgat   1080

tacgaggccg tggtcagcat caactacaac agtgctcagt acaagacggt aaacaacacc   1140

tggaaaccat ggaatcggat agacaacaac actgacgggt atgatggaat gatattcggg   1200

gacaaattga tcatcccaga catcgagaaa taccagagca tctatgacag cggaatgctt   1260

gttcaaagaa acctggtgga aattccccat ccgagcattg tgttcgtctc caacacatct   1320

gatctctcca ctaactacat ccacaccaat ctaattcctt cggattggtc attcaattgg   1380

agtctttggc cgtcactatc aggaatgggg gtagtgggag gggccttcct tctgctcgtg   1440

ctctgctgtt gctgcagggc atctccccct cctccgagtt acgggattcc gatgcagcag   1500

ttctccagaa gccagatggt ctga                                          1524


<210> SEQ ID NO 30
<211> LENGTH: 1575
<212> TYPE: DNA
<213> ORGANISM: Artificial Sequence
<220> FEATURE:
<223> OTHER INFORMATION: VHSV_KR2002

<400> SEQUENCE: 30

atggaatgta atactttttt cttggtgatt ctgatcatca tcataaaaag caccacatca     60
```

```
cagatcactc aacgacctcc ggtcgagaac atctcaacat accatgtaga ctgggacact    120
ccactgtata ctcacccctc caactgcaga aaaaactcct ttgttccgat tcggccagat    180
caactcaggt gtccccatga gttcgaggac acaaacaagg gcttggtctc tgtcccagcc    240
cagatcatcc atcttccgtt atcagtcacc ggcgtctcag cagtcgcaaa tggccactac    300
ctacacagag tgacctaccg ggtcacctgc tcaaccaatt tctttggagg acaaaccatt    360
gaaaaaacca tcctggaggc aaagctgtcc cgtcaagagg ccatcaatga ggctggcaag    420
gatcacgagt accctttctt ccccgaacct tcctgcatct ggatgaagga caatgtccac    480
aaggacataa cccactatta caagacccca aagacggtgt ccattgatct ctacagtaga    540
aagtttctaa accctgactt catagagggg gtttgtacaa catcaccctg cccaacccac    600
tggcaaggag tctactggat cggtgctaca cctcaggccc attgccctac ctcagaaacg    660
cttaaggggc atctgttcac caggacacat gatcacaggg tggtcaaggc aatcgttgcg    720
ggtcaccacc cctgggggct cacaatggca tgcacggtga cattttgtgg gacagaatgg    780
atcaagaccg acctgggga ccttattcag gtgacagggc agggggagc gaagaaactg     840
tctccaaaga agtgtgtcaa caccgacgtt cagatgaggg gagccacaga cgacttctct    900
tatcttaacc atctcattac caacatggct caaagaactg agtgcctgga cgcccacagt    960
gatatcactg cctctgggaa gatatcccct tttctcctct caaagtttcg tcctagtcac   1020
ccggggccgg gcaaggcaca ttatctcctt gatggccaga tcatgcgagg tgagtgtgat   1080
tacgaggccg tggtcagcat caactacaac agtgctcagt acaagacggt aaacaacatc   1140
tggaaaccat gggataggat agacaacaac actgacgggt atgacggaat gatattcggg   1200
gacaaattga tcatcccaga catcgagaaa taccagagca tctatgacag cggaatgctt   1260
gttcaaagaa acctggtgga aattccccat ccgagcattg tgttcgtctc aaacacatct   1320
gatctctcca ctaaccacat ccacaccaat ctaattcctt cggattggtc attcaaatgg   1380
agtctttggc cgtcactatc aggaatgggg gtagtgggag gggccttcct tctgctcgtg   1440
ctctgctgtt gctgcagggc atctccccct cctccgagtt acgggattcc gatgcagcag   1500
ttctccagaa gccagatggt ctgagcacac ccgcctaaac caccatagtt tccctcttag   1560
gtagatagaa aaaaa                                                    1575
```

<210> SEQ ID NO 31
<211> LENGTH: 1524
<212> TYPE: DNA
<213> ORGANISM: Artificial Sequence
<220> FEATURE:
<223> OTHER INFORMATION: VHSV_IVaJF00Ehi1Japan

<400> SEQUENCE: 31

```
atggaatgga atactttttt cttggtgatt ctgatcatca tcataaaaag caccacatca     60
cagatcactc aacgacctcc ggtcgagaac atctcaacat accatgtaga ctgggacact    120
ccactgtata ctcatccctc caactgcaga aaaaactcct ttgttccgat tcggccagct    180
caactcaggt gtccccatga gttcgaggac acaaacaagg gcttggtctc tgtcccagcc    240
cagatcatcc atcttccgtt atcagtcacc agcgtctcag cagtcgcaaa tggccactac    300
ctacacagag tgacctaccg ggtcacctgc tcaaccaatt tctttggagg acaaaccatt    360
gaaaaaacca tcctggaggc aaagctgtcc cgtcaagagg ccatcaatga ggctggcaag    420
gatcacgagt accctttctt ccccgaacct tcctgcatct ggatgaagga caatgtccac    480
aaggacataa cccactatta caagacccca aagacagtgt ccattgatct ctacagtaga    540
```

aagtttctaa accctgactt catagagggg gtttgtacaa catcaccctg cccaacccac 600
tggcaaggag tctactggat cggcgctaca cctcaggccc attgccctac ctcagaaacg 660
cttaaggggc atctgttcac caggacacat gatcacaggg tggtcaaggc aatcgttgcg 720
ggtcaccacc cctgggggct cacaatggca tgcacggtga cattttgtgg gacagaatgg 780
atcaagaccg acctggggga ccttattcag gtgacagggc agggggagc gaagaaactg 840 tctccaaaga agtgtgtcaa caccgacgtt cagatgaggg gagccacaga cgacttctct 900
tatcttaacc atctcattac caacatggct caaagaactg agtgcctgga cgcccacagt 960
gatatcactg cctctgggaa gatatcccct tttctcctct caaagtttcg tcctagtcac 1020
ccggggccgg gcaaggcaca ttatctcctt gatggccaga tcatgcgagg tgagtgtgat 1080
tacgaggccg tggtcagcat caactacaac agtgctcagt acaagacggt aaacaacatc 1140
tggaaaccat ggaatcggat agacaacaac actgacgggt atgatggaat gatattcggg 1200
gacaaattga tcatcccaga catcgagaaa taccagagca tctatgacag cggaatgctt 1260
gttcaaagaa acctggtgga aattccccat ccgagcattg tgttcgtctc caacacatct 1320
gatctctcca ctaaccacat ccacaccaat ctaattcctt cggattggtc attcaattgg 1380
agtctttggc cgtcactatc aggaatgggg gtagtgggag gggccttcct tctgctcgtg 1440
ctctgctgtt gctgcagggc atctcccccct cctccgagtt acgggattcc gatgcagcag 1500
ttctccagaa gccagatggt ctga 1524

<210> SEQ ID NO 32
<211> LENGTH: 1575
<212> TYPE: DNA
<213> ORGANISM: Artificial Sequence
<220> FEATURE:
<223> OTHER INFORMATION: VHSV_IVaJP99Obama25Japan

<400> SEQUENCE: 32
atggaatgga atactttttt cttggtgatt ctgatcatca tcataaaaag caccacatca 60
cagatcactc aacgacctcc ggtcgagaac atctcaacat accatgtaga ctgggacact 120
ccactgtata ctcacccctc caactgcaga aaaaactcct ttgttccgat tcggccagct 180
caactcaggt gtccccatga gttcgaggac acaaacaagg gcttggtctc tgtcccagcc 240
cagatcatcc atcttccgtt atcagtcacc agcgtctcag cagtcgcaaa tggccactac 300
ctacacagag tgacctaccg ggtcacctgc tcaaccaatt tctttggagg acaaaccatt 360
gaaaaaacca tcctggaggc aaagctgtcc cgtcaagagg ccatcaatga ggctggcaag 420
gatcacgagt accctttctt ccccgaacct tcctgcatct ggatgaagga caatgtccac 480
aaggacataa cccactatta caagacccca aagacagtgt ccattgatct ctacagtaga 540
aagtttctaa accctgactt catagagggg gtttgtacaa catcaccctg cccaacccac 600
tggcaaggag tctactggat cggcgctaca cctcaggccc attgccctac ctcagaaacg 660
cttaaggggc atctgttcac caggacacat gatcacaggg tggtcaaggc aatcgttgcg 720
ggtcaccacc cctgggggct cacaatggca tgcacggtga cattttgtgg gacagaatgg 780
atcaagaccg acctggggga ccttattcag gtgacagggc agggggagc gaagaaactg 840 tctccaaaga agtgtgtcaa caccgacgtt cagatgaggg gagccacaga cgacttctct 900
tatcttaacc atctcattac caacatggct caaagaactg agtgcctgga cgcccacagt 960
gatatcactg cctctgggaa gatatcccct tttctcctct caaagtttcg tcctagtcac 1020

```
ccggggccgg gcaaggcaca ttatctcctt gatggccaga tcatgcgagg tgagtgtgat   1080

tacgaggccg tggtcagcat caactacaac agcgctcagt acaagacggt aaacaacatc   1140

tggaaaccat ggaatcggat agacaacaac actgacgggt atgatggaat gatattcggg   1200

gacaaattga tcatcccaga catcgagaaa taccagagca tctatgacag cggaatgctt   1260

gttcaaagaa acctggtgga aattccccat ccgagcattg tgttcgtctc caacacatct   1320

gatctctcca ctaaccacat ccacaccaat ctaattcctt cggattggtc attcaattgg   1380

agtctttggc cgtcactatc aggaatgggg gtagtgggag gggccttcct tctgctcgtg   1440

ctctgctgtt gctgcagggc atctccccct cctccgagtt acgggattcc gatgcagcag   1500

ttctccagaa gccagatggt ctgagcacac ccgcctaaac caccatagtt tccctcttag   1560

gtagatagaa aaaaa                                                    1575
```

<210> SEQ ID NO 33
<211> LENGTH: 1575
<212> TYPE: DNA
<213> ORGANISM: Artificial Sequence
<220> FEATURE:
<223> OTHER INFORMATION: VHSV_IVaMakahUSA

<400> SEQUENCE: 33

```
atggaatgta atactttttt cttggtgatt ctgatcatca tcataaaaag caccacatca     60

cagatcactc aacgacctcc ggtcgagaac atctcaacat accatgcaga ctgggacact    120

ccactgtata ctcacccttc caactgcaga aaaaactcct ttgttccgat tcggccagct    180

caactcaggt gtccccatga gttcgaggac acaaacaagg gcttggtctc tgtcccagcc    240

cagatcatcc atcttccgtt atcagtcacc agcgtctcag cagtcgcaaa tggccactac    300

ctacacagag tgacctaccg ggtcacctgc tcaaccagtt tctttggagg acaaaccatt    360

gaaaaaacca tcctggaggc aaagctgtcc cgtcaagagg ccaccaatga ggccggcaag    420

gatcacgagt accctttctt ccccgaacct tcctgcatct ggatgaagga caatgtccac    480

aaggacataa cccactatta caagacccca aagacagtgt ccattgatct ctacagtaga    540

aagtttctaa accctgactt catagagggg gtttgtacaa catcaccctg cccaacccac    600

tggcaaggag tctactggat cggcgctaca cctcaggccc attgccctac ctcagaaacg    660

cttaaggggc atctgttcac caggacacat gatcacaggg tggtcaaggc aatcgttgcg    720

ggtcaccacc cctgggggct cacaatggca tgcacggtga cattttgtgg gacagaatgg    780

atcaggaccg acctgggggga ccttattcag gtgacagggc agggggagc gaagaaactg    840

tctccaaaga agtgtgtcaa caccgacgtt cagatgaggg gagccacaga cgacttctct    900

tatcttaacc atctcattac caacatggct caaagaactg agtgcctgga cgcccacagt    960

gatatcactg cctctgggaa gatatcccct tttctcctct caaagtttcg tcctagtcac   1020

ccgggacctg gcaaggcaca ttatctcctt gatggccaga tcatgcgagg tgagtgtgat   1080

tacgaggccg tggtcagcat caactacaac agtgctcagt acaagacggt aaacaacacc   1140

tggaaaccat ggaatcggat agacaacaac actgacgggt atgatggaat gatattcggg   1200

gacaaattga tcatcccaga catcgagaaa taccagagca tctatgacag cggaatgctt   1260

gttcaaagaa acctggtgga aattccccat ccgagcattg tgttcgtctc caacacatct   1320

gatctctcca ctaaccacat ccacaccaat ctaattcctt cggattggtc attcaattgg   1380

agtctttggc cgtcactatc aggaatgggg gtagtgggag gggccttcct tctgctcgtg   1440

ctctgctgtt gctgcagggc atctccccct cttccgagtt acgggattcc gatgcagcag   1500
```

ttctccagaa gccagatggt ctgagcacac ccgcctaaac caccatagtt tccctcttag 1560
gtagatagaa aaaaa 1575

<210> SEQ ID NO 34
<211> LENGTH: 1524
<212> TYPE: DNA
<213> ORGANISM: Artificial Sequence
<220> FEATURE:
<223> OTHER INFORMATION: VHSV_IVbCANB0201

<400> SEQUENCE: 34
atggaatgga atactttttt cttggtgatt ctgataatca tcataaaaag caccacatca 60
cagatcactc aacgacctcc ggtcgagaat atctcaacat accatgcaga ttgggacact 120
ccactgtata ctcacccttc caactgtaga aaagactcct ttgttccgat tcgaccagct 180
caactcaggt gtcctcatga attcgaggac ataaacaagg gcttggtctc tgtcccaact 240
cagatcatac atcttccgct atcagtcaca agcgtctcag cagttgcaag tggccactac 300
ctacacagag tgacctaccg agtcacctgc tcaaccggtt tttttggagg acaaaccatt 360
gagaagacca tcctggaagc aaagctgtcc cgtcaagagg ccgccaatga ggccggcaag 420
gatcacgagt acccgttctt ccccgaacct tcctgcatct ggatgaagga caatgtccac 480
aaggacataa cccactatta caagacccca aagacagtgt ccatcgatct ctacagtaga 540
aagtttctaa accctgactt catagagggg gtctgtacaa catcaccctg cccaacccac 600
tggcaaggag tctactggat cggcgccaca cctcaggccc attgccccac ctcagaaacg 660
cttgaggggc atctgttcac caggacacat gatcacaggg tggtcaaggc aatcgtggca 720
ggtcaccacc cctgggggct cacaatggca tgcacggtga cattttgtgg gacagaatgg 780
atcaagaccg acctggggga ccttattcag gtgacaggac agggggagc gaagaaactg 840 tctccaagga agtgtgtcaa caccaacatt cagatgaggg gagccacaga cgacttctct 900
taccttgacc atctcatcac caacatggct caaagaactg agtgcctgga cgcccacagt 960
gatatcactg cctctgggaa gatctcctcc tttctcctct caaagtttcg tcccagtcac 1020
ccggggccgg gcaaggcaca ttatctcctt gatggccaga tcatgcgagg tgagtgtgac 1080
tatgaggccg tggtcagcat caactacaac agtgctcagt acaagacggt aaacaacacc 1140
tggaaatcat ggaatcggat agacaacaac actgacgggt atgatggaat gatattcggg 1200
gacaaattga tcatcccaga catcgagaaa taccagagca tctatgacag tggaatgctc 1260
gttcaaagga acctggtgga aattccccat ctgagtattg tgttcgtctc caacacatct 1320
gatctctcca ctaaccacat ccacaccaat ctaattcctt cggattggtc gttcaattgg 1380
agtctttggc cgtcactatc aggaatgggg gtagtgggag gggccttcct tctactagtg 1440
ctctgctgtt gctgcaaggc atctcctcct cttccgagtt acgggattcc gatgcagcag 1500
ttctccagaa gccagatggt ctga 1524

<210> SEQ ID NO 35
<211> LENGTH: 1524
<212> TYPE: DNA
<213> ORGANISM: Artificial Sequence
<220> FEATURE:
<223> OTHER INFORMATION: VHSV_Id2375

<400> SEQUENCE: 35
atggaatgga acactttttt cttggtgatc ttgatcatca tcataaagag caccacacca 60

-continued

```
cagatcactc aacgacctcc ggtcgaaaac atctcgacgt accatgcaga ttgggacact    120
ccgctataca ctcatccctc caactgcagg gacgattcct ttgtcccgat tcgaccagct    180
caactcaggt gtcctcatga atttgaagac ataaacaagg gactggtttc cgtcccaacc    240
cagatcatcc atctcccgct atcagtcacc agcgtctccg cagtagcgag tggccactac    300
ctgcacagag tgacttatcg agtcacctgt tcgaccagct tctttggagg gcaaaccatc    360
gaaaagacca tcttggaggc gaaactgtct cgtcaggagg ccacaaacga ggcaagcaag    420
gatcacgagt acccgttctt ccctgaaccc tcctgcatct ggatgaaaaa caatgtccat    480
aaggacataa ctcactatta caagacccca aaaacagtat cggtggatct ctacagcaga    540
aaatttctca accctgattt catagagggg gtttgcacaa cctcgccctg tcaaactcat    600
tggcagggag tctattgggt cggtgccacc cctacagccc attgccccac gtcggaaaca    660
ctagaaggac acctgttcac caggacccat gatcacaggg tggtcaaggc aattgtggca    720
ggccatcatc cctggggact cacaatggca tgcacagtga cattctgcgg gacagactgg    780
atcaagaccg acctggggga cctgatcaag gtgacaggac cgggggcac gaggatactg    840
actccacgga agtgtgtcaa tgccgatgtc cagatgaggg gggcaacgga cgacttttct    900
tatctcaacc atctcatcac caacatggct caaagaaccg agtgcctaga tgcccatagt    960
gatatcaccg cttctgggaa aatatcccca tttctcctct caaagtttcg tcccagccac   1020
cctggacccg gcaaggcaca ctatcttctc gacggtcaaa tcatgcgagg tgactgtgac   1080
tatgaggcag tagtcagcat caactacaat agcgctcaat acaagacggt gaacaacaca   1140
tggaaatcat ggaaacgggt agacaacaac acagacgggt acgatgggat gatatttggg   1200
gacaaattga tcatcccgga catcgagaag tatcagagtg tctatgacag tggaatgctc   1260
gttcaaagaa accttgtgga agtccctcat ctgagcattg tgtttgtctc caacacatct   1320
gatctttcca ccaatcacat ccacaccaac ctaatccctt cggattggtc attcaactgg   1380
agtctttggc catcattatc tgggatgggg gttgtgggag ggccctcct tctactggta   1440
ctctgctgtt gctgcaaggc gtcccctccc attccaaatt acgggactcc gatgcagcag   1500
ttctctagaa gtcagacggt ctga                                          1524
```

<210> SEQ ID NO 36
<211> LENGTH: 1524
<212> TYPE: DNA
<213> ORGANISM: Artificial Sequence
<220> FEATURE:
<223> OTHER INFORMATION: VHSV_IIDK1p52

<400> SEQUENCE: 36

```
atggaatgga atactttttt cttagtgatt ttgatcatca tcataaaaag caccacgtca     60
cagatcactc aacgacctcc ggccgagaac atctcaactt accatgcaga ttgggacact    120
ccactataca ctcatccctc caactgcagg gaagattcct ttgtccctat tcgaccagct    180
caactaaggt gtcctcatga atttgaagac ataaacaagg gattggtatc cgtccctact    240
cagattgttc atctcccgtt atcagtcact agcgtctccg cagttgcaag tggtcactac    300
ctgcacagag tgacctatcg agtcacctgc tcaaccagct tctttggagg gcaaaccatc    360
gaaaagacca tcctggaagc gaagctgtct cgtcaagagg ccatagatga ggcaagcaaa    420
gatcatgagt acccgttctt tcctgaacct tcctgcattt ggatgaagaa caatgttcac    480
aaggacataa ctcactatta caagacccca agaacagtat ctgtcgacct ctatagcagg    540
aaatttctca accctgattt catagagggg gtttgtacga cctcgccttg tcagactcat    600
```

```
tggcagggag tctattgggt cggtgccaca cccacggctc attgtcccgt gtcagaaacg    660
ctagaaggac acctgttcac cagaacccat gatcataggg tggtcaaggc aatcgtggca    720
ggccatcacc cctggggact cacaatggca tgcacagtga cattctgtgg gacggagtgg    780
atcaagaccg acctgggga cctgatcaag gtgacagtgc agggggtga gcagaaactg    840
actccggaaa agtgtattaa caccgacgtt cagatgaggg gggcaacgga cgacttctcc    900
tatctcggcc atctcatcac taatatggct caaagaactg agtgcctaga tgctcacagt    960
gacatcactg cctctgggaa gatatcttct tttctcctat caaagttccg tcccaatcac   1020
cctggacccg gtaaggcaca ctatcttctt gatggtcaga tcatgcgagg tgactgtgac   1080
tatgaggcgg tagtcagcat caactacaac agcgctcaat acaagacggt gaacaacacc   1140
tggaaatcat ggaagcggat aggcaacaac acagatgggt acgatgggat gatatttggg   1200
gacaagctgg taatcccaga catcgagaaa tatcagagca tctatgacag tggaatgctc   1260
gttcaaagaa acctggcaga agttcctcat ctgagcgttg tgtttgtctc caacacatcc   1320
gatctttcca ccaattacat ccacaccaat ctgatccctt cagattggtc cttcaactgg   1380
agcctttggc cgtcgttatc tgggatggga gtcgtgggag tgatcctcct tctgctgata   1440
ttctgttgtt gctgcaaagc gtcccctccc attccaaact atgggattcc tatgcagcaa   1500
ttctccagaa accagatgat ctga                                          1524
```

<210> SEQ ID NO 37
<211> LENGTH: 1524
<212> TYPE: DNA
<213> ORGANISM: Artificial Sequence
<220> FEATURE:
<223> OTHER INFORMATION: VHSV_IIIDK4p168

<400> SEQUENCE: 37

```
atggaatgga atactttttt cttggtgatc ttgatcattc tcataaagag caccacatca     60
cagatcaccc aaagacctcc gatcgagaac atctcgacgt accatgcaga ttgggacact    120
ccgttgtaca ctcacccctc caactgcaga gaagactcct ttgtcccgat tcgaccagct    180
caactcaggt gtcctcatga atttgaagac atcaacaagg gactggtctc cgttccaact    240
cagatcattc atctcccgct atcagtcacc agcgtctccg cagttgcaag tggccactac    300
ctgcacagag tgacctatcg agtcacctgc tcaaccagct tctttggggg acaaaccatc    360
gaaaagacca tcctggaagc aaaattgtct cgtcaggagg ccgcaaatga ggcaagcaaa    420
gaccatgagt acccgttctt tcctgaaccc tcctgcatct ggatgaaaaa taatgtccat    480
aaggatataa ctcactatta taagacccca aaaacagtct ctgtggatct ctacagcagg    540
aaatttctta accctgattt catagagggg gtttgtacga cctcgccctg tcagactcat    600
tggcagggag tctattgggt cggtgccaca cccacagccc attgtcccac ttcagaaaca    660
ctagaggggc acctgttcac cagaactcat gatcacagag tggtcaaggc aattgtggcg    720
ggccatcacc catggggact cacgatggca tgcacagtga cattctgtgg gacagattgg    780
atcaagaccg acctgggga cctgatcaag gtggtaggac agggggcga aacaaaactg    840
actccaaaaa aatgtgtcaa tactgacatc cagatgaggg ggcaacaga cgacttctcc    900
tatctcaacc atctcatcac aaacatggct caaaggaccg agtgtctaga cgcccatagt    960
gacatcactg cctccgggaa aatatcctcg tttctcctct caaagtttcg tcccagccac   1020
cccggacccg gcaaggcaca ttacctcctt gatggtctaa tcatgcgagg tgactgtgac   1080
```

```
tatgaggcgg tagtcagtat caactacaat agcgctcagt acaagacggt gaacaacaca   1140

tggaagtcat ggaaacggat agacaacaat acagatgggt acgatgggat gatatttgga   1200

gacaaactga tcatcccaga catcgagaaa tatcagagta tctatgatag tgggatgctt   1260

gttcaaagga acctggtgga agttcctcat ctgagcattg tgtttgtctc caacacatct   1320

gatctctcca ccaatcacat ccacaccaac ttaatcccct cggattggtc attcaactgg   1380

agcctctggc cgtcattatc agggatggga gttgtgggag ggccttcct tctattggtg   1440

ctttgctgtt gttgcaaagc gtctcctcct attccaaatt acgggattcc tatgcagcaa   1500

ttctccagaa atcagatggt ctga                                          1524
```

<210> SEQ ID NO 38
<211> LENGTH: 1524
<212> TYPE: DNA
<213> ORGANISM: Artificial Sequence
<220> FEATURE:
<223> OTHER INFORMATION: VHSV_IcDK5151

<400> SEQUENCE: 38

```
atggaatgga acactttctt cttggtgatc ttgatcatca tcataaagag caccacacca     60

cagatcactc aacgacctcc ggttgaaaac atctcgacgt accatgcaga ttgggacact    120

ccgctataca ctcatccctc caactgcagg gacgattcct ttgtcccgat tcgaccagct    180

caactcaggt gtcctcatga atttgaagac ataaacaagg gactggtttc cgtcccaacc    240

aagatcatcc atctcccgct atcagtcacc agcgtctccg cagtagcgag cggccactac    300

ctgcacagag tgacttatcg agtcacctgt tcgaccagct tctttggagg gcaaaccatt    360

gaaaagacca tcttggaggc gaaactgtct cgtcaggagg ccacagacga ggcaagcaag    420

gaccacgagt acccgttctt ccctgaaccc tcctgcatct ggatgaaaaa caatgtccat    480

aaggacataa ctcactatta caagacccca aaaacagtat cggtggatct ctacagcagg    540

aaatttctca accctgattt catcgaaggg gtctgcacaa cctcgccctg tcaaactcat    600

tggcagggag tctattgggt cggcgccaca cccaatgccc attgccccac gtcggaaaca    660

ctagaaggac acctgttcac caggacccat gatcacaggg tggtcaaggc aattgtggca    720

ggccatcatc cctggggact cacaatggca tgcacagtga cattctgcgg ggcagattgg    780

atcaagactg acctgggaga cctgatccag gtgacaggac cgggggcac ggggaaactg     840

actccaaata agtgtgtcaa tactgatgtc cagatgaggg gggcaacaga cgacttttct    900

tatctcaacc atctcatcac caacatggct caaagaaccg agtgcctaga tgcccatagt    960

gatatcaccg cttctgggaa aatatcctca tttctcctct caaagtttcg tcccagccac   1020

cctggacccg gcaaggcaca ctatcttcta gacggtcaaa tcatgcgagg tgactgtgac   1080

tatgaggcag tagtcagcat caactacaac agcgctcaat acaagacggt gaacaacaca   1140

tggaaatcat ggaaacgggt agacaacaac acagacgggt acgatgggat gatatttggg   1200

gacaaattga tcatcccgga catcgagaag tatcagagtg tctatgacag tggaatgctc   1260

gttcaaagaa accttgtgga agtccctcat ctgagcattg tgtttgtctc caacacatct   1320

gatctttcca ctaatcacat ccacaccaac ctaatccctt cggattggtc attccactgg   1380

agtctttggc cctcattgtc tgggatgggg gttgtgggag ggccttcct tctactggtg    1440

ctctgctgtt gctgcaaggc gtcccctcca actccaaact acgggattcc gatgcagcag   1500

ttctccagaa gtcagacggt ctga                                          1524
```

<210> SEQ ID NO 39
<211> LENGTH: 1575
<212> TYPE: DNA
<213> ORGANISM: Artificial Sequence
<220> FEATURE:
<223> OTHER INFORMATION: VHSV_IHededamDenmark70

<400> SEQUENCE: 39
atggaatgta atactttttt cttggtgatc ttgatcatca tcataaagag caccacacca 60
cagatcactc aacgacctcc ggtcgaaaac atctcgacgt accatgcaga ttgggacact 120
ccgctctaca ctcatccctc caactgcagg gaagattcct ttgtcccgat tcgaccagct 180
caactcaggt gtcctcatga atttgaagac ataaacaagg gactggtctc cgtcccaact 240
cagatcatcc atctcccgct atcagtcacc agcgtctccg cagtagcgag tggccactac 300
ctgcacagag tgacttatcg agtcacctgt tcgaccagct tctttggagg acaaaccatc 360
gaaaagacca tcttggaggc gaaattgtct cgtcaggagg ccacaaacga gggaagcaag 420
gatcacgagt acccgttctt ccctgaaccc tcctgcatct ggatgaaaaa caatgtccat 480
aaggacataa ctcactatta caagacccca aaaacagtat cggtggatct ctacagcagg 540
aaatttctca accctgattt catagagggg gtttgcacaa cctcgccctg tcaaactcat 600
tggcagggag tctattgggt cggtgccaca cctaaagccc attgccccac gtcggaaaca 660
ctagagggac acctgttcac caggacccat gatcacaggg tggtcaaggc aattgtggca 720
ggccatcatc cctggggact cacaatggca tgcacagtga cattctgcgg gacagactgg 780
atcaagaccg acctggggga cctgatcaag gtgacaggac cgggggggcgc gaggaaactg 840 actccaaaaa agtgtgtcaa tgccgacatc cagatgaggg ggcaacaga cgacttttct 900 tatctcaacc atctcatcac caacatggct caaagaaccg agtgcctaga tgcccatagt 960
gatatcaccg cttctgggaa aatatcctca tttctcctct caaagtttcg tcccagccac 1020
cctggacctg gcaaggcaca ctatcttctc gacggtcaaa tcatgcgagg tgactgtgac 1080
tatgaggcag tagtcagcat caactacaat agcgctcaat acaagacggt gaacaacaca 1140
tggaaatcat ggaaacgggt agacaacaac acagacgggt acgatgggat gatatttggg 1200
gacaaattga tcatcccgga catcgagaag tatcagagtg tctatgacag tggaatgctc 1260
gttcaaagaa accttgtgga agtccctcat ccgagcattg tgtttgtctc caacacatcc 1320
gatctttcca ctaatcacat ccaaaccaac ctaatccctt cggattggtc attcaactgg 1380
agtctttggc catcattatc tgggatgggg gttgtgggag gggccctctc tctactggta 1440
ctctgctgtt gctgcaaggc gtcccctcct attccaaatt acgggattcc gatgcagcag 1500
ttctccagaa gtcagacggt ctgagcacac ctgtccgaat gaccacaatt cctctcttag 1560
gtagatagaa aaaaa 1575

<210> SEQ ID NO 40
<211> LENGTH: 1524
<212> TYPE: DNA
<213> ORGANISM: Artificial Sequence
<220> FEATURE:
<223> OTHER INFORMATION: VHSV_IaFR0771

<400> SEQUENCE: 40
atggaatgga acactttctt cttggtgatc ttgatcatca tcataaagag caccacacca 60
cagatcactc aacgacctcc ggttgaaaac atctcgacgt accatgcaga ttgggacact 120
ccgctataca ctcatccctc caactgcagg gacgattcct ttgtcccgat tcgaccagct 180

-continued caactcaggt gtcctcatga atttgaagac ataaacaagg gactggtttc cgtcccaacc 240
aagatcatcc atctcccgct atcagtcacc agcgtctccg cagtagcgag cggccactac 300
ctgcacagag tgacttatcg agtcacctgt tcgaccagct tctttggagg gcaaaccatt 360
gaaaagacca tcttggaggc gaaactgtct cgtcaggagg ccacagacga ggcaagcaag 420
gaccacgagt acccgttctt ccctgaaccc tcctgcatct ggatgaaaaa caatgtccat 480
aaggacataa ctcactatta caagacccca aaaacagtat cggtggatct ctacagcagg 540
aaatttctca accctgattt catcgaaggg gtctgcacaa cctcgccctg tcaaactcat 600
tggcagggag tctattgggt cggcgccaca cccaatgccc attgccccac gtcggaaaca 660
ctagaaggac acctgttcac caggacccat gatcacaggg tggtcaaggc aattgtggca 720
ggccatcatc cctggggact cacaatggca tgcacagtga cattctgcgg ggcagattgg 780
atcaagactg acctgggaga cctgatccag gtgacaggac cggggggcac ggggaaactg 840
actccaaata agtgtgtcaa tactgatgtc cagatgaggg gggcaacaga cgacttttct 900
tatctcaacc atctcatcac caacatggct caaagaaccg agtgcctaga tgcccatagt 960
gatatcaccg cttctgggaa aatatcctca tttctcctct caaagtttcg tcccagccac 1020
cctggacccg gcaaggcaca ctatcttcta gacggtcaaa tcatgcgagg tgactgtgac 1080
tatgaggcag tagtcagcat caactacaac agcgctcaat acaagacggt gaacaacaca 1140
tggaaatcat ggaaacgggt agacaacaac acagacgggt acgatgggat gatatttggg 1200
gacaaattga tcatcccgga catcgagaag tatcagagtg tctatgacag tggaatgctc 1260
gttcaaagaa accttgtgga agtccctcat ctgagcattg tgtttgtctc caacacatct 1320
gatctttcca ctaatcacat ccacaccaac ctaatccctt cggattggtc attccactgg 1380
agtctttggc cctcattgtc tgggatgggg gttgtgggag gggccttcct tctactggtg 1440
ctctgctgtt gctgcaaggc gtcccctcca actccaaact acgggattcc gatgcagcag 1500
ttctccagaa gtcagacggt ctga 1524

<210> SEQ ID NO 41
<211> LENGTH: 1524
<212> TYPE: DNA
<213> ORGANISM: Artificial Sequence
<220> FEATURE:
<223> OTHER INFORMATION: VHSV_strainKRRV9822

<400> SEQUENCE: 41
atggaatgga atactttttt cttggtgatt ctgatcatca tcataaaaag caccacatca 60
cagatcactc aacgacctcc ggtgcagaac atctcaacat accatgtaga ctgggacact 120
ccactgtata ctcacccttc caactgcaga aaaaactcct ttgttccgat tcggccagct 180
caactcaggt gtccccatga gttcgaggac acaaacaagg gcttggtctc tgtcccagcc 240
cagatcatcc atcttccgtt atcagtcacc agcgtctcag cagtcgcaaa tggccactac 300
ctacacagag tgacctaccg ggtcacctgc tcaaccaatt tctttggagg acaaaccatt 360
gaaaaaacca tcctggaggc aaagctgtcc cgtcaagagg ccatcaatga ggctggcaag 420
gatcacgagt accctttctt ccccgaacct tcctgcatct ggatgaagga caatgtccac 480
aaggacataa cccactatta caagacccca aagacagtgt ccattgatct ctacagtaga 540
aagtttctaa accctgactt catagagggg gtttgtacaa catcaccctg cccaacccac 600
tggcaaggag tctactggat cggcgctaca cctcaggccc attgccctac ctcagaaacg 660
cttaaggggc atctgttcac caggacacat gatcacaggg tggtcaaggc aatcgttgcg 720

```
ggtcaccacc cctgggggct cacaatggca tgcacggtga cattttgtgg gacagaatgg    780

atcaagaccg acctggggga ccttattcag gtgacagggc agggggggagc gaagaaactg    840

tctccaaaga agtgtgtcaa caccgacgtt cagatgaggg gagccacaga cgacttctct    900

tatcttaacc atctcattac caacatggct caaagaactg agtgcctgga cgcccacagt    960

gatatcactg cctctgggaa gatatcccct tttctcctct caaagtttcg tcctagtcac   1020

ccggggccgg gcaaggcaca ttatctcctt gatggccaga tcatgcgagg tgagtgtgat   1080

tacgaggccg tggtcagcat caactacaac agtgctcagt acaagacggt aaacaacatc   1140

tggaaaccat ggaatcggat agacaacaac actgacgggt atgatggaat gatattcggg   1200

gacaaattga tcatcccaga catcgagaaa taccagagca tctatgacag cggaatgctt   1260

gttcaaagaa acctggtgga aattccccat ccgagcattg tgttcgtctc caacacatct   1320

gatctctcca ctaaccacat ccacaccaat ctaattcctt cagattggtc attcaattgg   1380

agtctttggc cgtcactatc aggaatgggg gtagtgggag gggcctccct tctgctcgtg   1440

ctctgctgtt gctgcagggc atctcccccct cctccgagtt acgggattcc gatgcagcaa   1500

ttctccagaa gccagatggt ctga                                          1524
```

<210> SEQ ID NO 42
<211> LENGTH: 1575
<212> TYPE: DNA
<213> ORGANISM: Artificial Sequence
<220> FEATURE:
<223> OTHER INFORMATION: VHSV_strainME03USA

<400> SEQUENCE: 42

```
atggaatgga atactttttt cttggtgatt ctgatcatca tcataaaaag caccacatca     60

cagatcactc aacgacctcc ggtcgagaac atctcaacat accatgcaga ctgggacact    120

ccactgtata ctcacccttc caactgcaga aaaaactcct ttgttccgat tcggccagct    180

caactcaggt gtccccatga gttcgaggac acaaacaagg gcttggtctc tgtcccagcc    240

cagatcatcc atcttccgtt atcagtcacc agcgtctcag cagtcgcaaa tggccactac    300

ctacacagag tgacctaccg ggtcacctgc tcaaccagtt tctttggagg acaaaccatt    360

gaaaaaacca tcctggaggc aaagctgtcc cgtcaagagg ccaccaatga ggccggcaag    420

gatcacgagt accctttctt ccccgaacct tcctgcatct ggatgaagga caatgtccac    480

aaggacataa cccactatta caagacccca aagacagtgt ccattgatct ctacagtaga    540

aagtttctaa accctgactt catagagggg gtttgtacaa catcaccctg cccaacccac    600

tggcaaggag tctactggat cggcgctaca cctcaggccc attgccctac ctcagaaacg    660

cttcaggggc atctgttcac caggacacat gatcacaggg tggtcaaggc aatcgttgcg    720

ggtcaccacc cctgggggct cacaatggca tgcacggtga cattttgtgg gacagaatgg    780

atcaggaccg acctggggga ccttattcag gtgacagggc agggggggagc gaagaaactg    840

tctccaaaga agtgtgtcaa caccgacgtt cagatgaggg gagccacaga cgacttctct    900

tatcttaacc atctcattac caacatggct caaagaactg agtgcctgga cgcccacagt    960

gatatcactg cctctgggaa gatatcccct tttctcctct caaagtttcg tcctagtcac   1020

ccggggccgg gcaaggcaca ttatctcctt gatggccaga tcatgcgagg tgagtgtgat   1080

tacgaggccg tggtcagcat caactacaac agtgctcagt acaagacggt aaacaacacc   1140

tggaaatcat ggaatcggat agacaacaac actgacgggt atgatggaat gatattcggg   1200
```

-continued

```
gacaaattga tcatcccaga catcgagaaa taccagagca tctatgacag cggaatgctt   1260

gttcaaagaa acctggtgga aattccccat ccgagcattg tgttcgtctc caacacatct   1320

gatctctcca ctaaccacat ccacaccaat ctaattcctt cggattggtc atccaattgg   1380

agtctttggc cgtcactatc aggaatgggg gtagtgggag gggccttcct tctgctcgtg   1440

ctctgctgtt gctgcagggc atctccccct cttccgagtt acgggattcc gatgcagcag   1500

ttctccagaa gccagatggt ctgagcacac ccgcctaaac caccatagtt tccctcttag   1560

gtagatagaa aaaaa                                                    1575
```

<210> SEQ ID NO 43
<211> LENGTH: 1524
<212> TYPE: DNA
<213> ORGANISM: Artificial Sequence
<220> FEATURE:
<223> OTHER INFORMATION: VHSV_1968_NOA16368G

<400> SEQUENCE: 43

```
atggaatgga atactttttt cttggtgatc ttgatcatca tcataaagag caccacacca     60

cagatcactc aacgacctcc ggtcgaaaac atctcgacgt accatgcaga ttgggacact    120

ccgctataca ctcatccctc caactgcagg gaagattcct ttgtcccgat tcgaccagct    180

caactcaggt gtcctcatga atttgaagac ataaacaagg gactggtttc cgtcccaact    240

cagatcatcc atctcccgct atcagtcacc agcgtctccg cagtagcgag tggccactac    300

ctacacagag tgacttatcg agtcacctgt tcgaccagct tctttggagg gcaaaccatc    360

gaaaagacca tcttggaggc gaaattgtct cgtcaggagg ccacaaacga ggcaagcaag    420

gatcacgagt acccgttctt ccctgaaccc tcctgcatct ggatgaagaa caatgtccat    480

aaggacataa ctcactatta caagacccca aaaacagtat cggtggatct ctacagcagg    540

aaatttctca accctgattt catagagggg gtttgcacaa cctcgccctg tcaaactcat    600

tggcagggag tctattgggt cggtgccaca cctacagccc attgccccac gtcggaaaca    660

ctagaaggac acctgttcac caggacccat gatcacaggg tggtcaaggc aattgtggca    720

ggccatcatc cctggggact cacaatggca tgcacagtga cattctgcgg ggtagaatgg    780

atcaagaccg acctggggga cctgatccag gtgacagaac cgggggggcgc gaggaaactg    840

actccaaaaa agtgtgtcaa tgccgatatc cagatgaggg ggcaacaga cgacttttct    900

tatctcaacc atctcatcac caacatggct caaagaaccg agtgcctaga tgcccatagt    960

gatatcaccg cttctggaaa aatatcctca tttctcctct caaagtttcg tcccagccac   1020

cctggacccg gcaaggcaca ctatcttctc gacggtcaaa tcatgcgagg tgactgtgac   1080

tatgaggcag tagtcagcat caactacaat agcgctcaat acaagacggt gaacaacaca   1140

tggaaatcat ggaaacgggt agacaacaac acagacgggt acgatgggat gatatttggg   1200

gacaaattga tcatcccgga catcgagaag tatcagagtg tctatgacag tggaatgctc   1260

gttcaaagaa accttgtgga agtccctcat ctgagcattg tgtttgtctc caacacatct   1320

gatctttcca ctaatcacat ccacaccaac ctaatccctt cggattggtc attcaactgg   1380

agtctttggc catcattatc tgggatgggg gttgtgggag gggccttcct tctactggta   1440

ctctgctgtt gctgcaaggc gtcccctcct attccaaatt acgggattcc gatgcagcag   1500

ttctccagaa gtcagacggt ctga                                          1524
```

<210> SEQ ID NO 44
<211> LENGTH: 20

-continued

```
<212> TYPE: DNA
<213> ORGANISM: Artificial Sequence
<220> FEATURE:
<223> OTHER INFORMATION: VHSV G protein 741-760 region
<220> FEATURE:
<221> NAME/KEY: misc_feature
<222> LOCATION: (4)..(4)
<223> OTHER INFORMATION: n can be a or g
<220> FEATURE:
<221> NAME/KEY: misc_feature
<222> LOCATION: (15)..(15)
<223> OTHER INFORMATION: n can be c or a
<220> FEATURE:
<221> NAME/KEY: misc_feature
<222> LOCATION: (16)..(16)
<223> OTHER INFORMATION: n can be a or g

<400> SEQUENCE: 44

cacnatggca tgcanngtga                                              20
```

PROBES FOR IDENTIFYING GEOGRAPHICAL DISTRIBUTION AND MOLECULAR EPIDEMIOLOGY OF VIRAL HEMORRHAGIC SEPTICEMIA VIRUS (VHSV) AND USES THEREOF

CROSS-REFERENCE TO RELATED APPLICATIONS

This application is a U.S. national phase under the provisions of 35 U.S.C. § 371 of International Patent Application No. PCT/KR2016/008830 filed Aug. 11, 2016, which in turn claims priority of Korean Patent Application No. 10-2015-0116166 filed Aug. 18, 2015. The disclosures of such international patent application and Korean priority patent application are hereby incorporated herein by reference in their respective entireties, for all purposes.

TECHNICAL FIELD

The present invention relates to a probe for identifying the geographical origin of viral hemorrhagic septicemia virus (VHSV), which is a fish pathogenic virus, and a method of identifying the geographical origin of VHSV using the same, and more particularly, to a method of identifying the geographical origin of VHSV in a simple, rapid and accurate manner, in which a PNA having a high binding affinity for a DNA containing C755A and A756G single-nucleotide polymorphisms (SNPs) of VHSV G-protein, which are genotypes appearing depending on the geographical origin of VHSV, is used so as to exhibit different melting temperatures depending on genotypes.

BACKGROUND ART

Viral hemorrhagic septicemia virus (VHSV) is known as a pathogen that infects freshwater salmonid fishes, including *Oncorhynchus mykiss*, to cause serious viral diseases. The VHSV is an about 11,000-bp negative-strand RNA virus belonging to the genus *Novirhabdovirus* of the family Rhabdoviridae, together with other fish viruses (infectious hematopoietic necrosisvirus (IHNV) and hirame rhabdovirus (HIRRV)), and comprises six genes, i.e., nucleocapsid (N), phosphoprotein (P), matrix protein (M), glycoprotein (G), non-virion protein (NV), and polymerase (L) in the order of 3'-N-P-M-G-NV-L-5' (Schutze et al., 1999; van Regenmortel et al., 2000; Trdo et al., 2005).

Since VHSV was first isolated from *Oncorhynchus mykiss* in Denmark in 1963 (Jensen, 1965; Wolf, 1988), it has been isolated from *Gadus morhua* (Jensen et al., 1979), *Scophthalmus maximus* (Schlotfeldt et al., 1991), *Clupea harengus* (Dixon et al., 1997), *Merlangius merlangus* (Mortensen et al., 1999) and the like in the Atlantic Ocean and the North Sea. The VHSV is known as a pathogen that causes diseases in both freshwater and seawater fishes. The VHSV was isolated from seawater fish and anadromous salmon not only in the European region, but also from the Western shore of the North America region in the latter half of 1980s, indicating that the virus is widely distributed in the marine environment (Hopper, 1989; Meyers and Winton, 1995).

In the Eastern Asia region, the VHSV was first detected in wild *Paralichthys olivaceus* in Wakasa Bay, Japan (Takano et al., 2000), after which damage to cultured *Paralichthys olivaceus* by VHSV was also reported (Isshiki et al., 2001). In South Korea, rhabdovirus diseases in cultured *Paralichthys olivaceus* prevail at similar times. A virus that causes the rhabdovirus diseases was examined, and as a result, it was found that the virus had the same genotype as that of the VHSV isolated from the North America region and Japan (Kim et al., 2003). Since then, the VHSV has been isolated from various seawater fishes and freshwater fishes, and the VHSV was reported to be a pathogen that annually causes the death of cultured *Paralichthys olivaceus* (Kim et al., 2004; Kim et al., 2009; Cho et al., 2012).

At present, the VHSV is classified as a notifiable disease by the Aquatic Animal Health Code of the World Organization for Animal Health (OIE) (OIE, 2013). In South Korea, the VHSV is an infectious aquatic organism disease stated in Article 2 of the Aquatic Life Disease Control Act, and is included in diseases to be subjected to preventive measures, and when the outbreak of VHSV infection and disease is detected, restriction on movement and disinfection action are needed. In recent years, due to the outbreak of various aquatic organism diseases and the increasing consumer's demand for food safety, the importance of aquatic animal disease control, surveillance and monitoring has increased worldwide. In addition, not only national surveillance and control actions, but also analysis of the results of surveillance and monitoring of regional and zoned aquatic organism diseases, play a very important role not only in providing useful data required for epidemiological investigation of aquatic organism diseases and disease control, but also in demonstrating a region free of a specific disease in the corresponding country (FAO, 2004). Thus, continued studies on sequence mutations of Korean VHSV isolates, sequence comparison with VHSV isolates isolated from other countries, and continued monitoring of VHSV, became more important.

The nucleotide sequences of the N and G genes of VHSV isolates identified worldwide were phylogenetically compared. As a result, it was found that these genes contained four genotype (I-IV) and several subgroups of genotype I (Ia to Ie) and genotype IV (IVa and IVb) (Snow et al., 1999; Einer-Jensen et al., 2004; Lumsden et al., 2007). Genotype I includes VHSV isolates isolated from various freshwater and seawater fishes in Europe and also includes many VHSV isolates isolated from seawater fishes in Baltic Sea, Skagerrak, Kattegat and English Channel (Dixon et al., 1997; Thiery et al., 2002; Einer-Jensen et al., 2004; Snow et al., 2004). Genotype II includes VHSV isolates isolated from seawater fishes in Baltic Sea (Snow et al., 2004), and genotype III includes VHSV isolates isolated from the North Sea and North Atlantic of England and Ireland and VHSV isolates isolated from rainbow trout in Western Norway (Einer-Jensen et al., 2004; Snow et al., 2004; Lopez-Vazquez et al., 2006; Dale et al., 2009). Genotype IV includes VHSV isolates isolated not only from North America's Pacific coast and Atlantic coast, but also from North America's Great Lakes region and the Asian region (Nishizawa et al., 2002; Kim et al., 2003; Elsayed et al., 2006; Gagne et al. 2007; Lumsden et al. 2007). Thus, it appears that the results of analysis of the genetic distance of VHSV and the results of phylogenetic analysis of VHSV are more related to geographical positions than host fish species.

Various methods for analyzing bacterial genotypes have been developed, and Sanger sequencing, random amplified polymorphic DNA (RAPD), restriction fragment length polymorphism (RFLP) techniques and the like have been used. However, these methods have still problems in that the analysis time is lengthy and analysis procedures are complicated. Additionally, the development of genotype and genetic markers that indicate pathogenicity is required. In addition, in order to analyze the pathogenicity depending on the genotype to determine the correlation therebetween, the development of genotype and genetic markers for rapid and convenient analysis and a method capable of easily identifying genetic markers is required.

In a previous study, the present inventors performed phylogenetic comparison of VHSV isolates isolated from Asia (J. Fish Pathol., 26(3):149-161). The results of the study revealed that Korean VHSV isolates had C-to-A mutation at residue 755 in the nucleotide sequence of the VHSV G-protein gene. However, in the above-described study, all the full-length open reading frames of the G-proteins of the VHSV isolates were amplified, and then the amplification products were cloned, and the purified plasmid DNAs were sequenced. Thus, there was a disadvantage in that large amounts of time and material are required.

Generally, peptide nucleic acid (PNA) is a DNA analogue having nucleic acid nucleotides connected by peptide bonds instead of phosphate bonds, and was first synthesized by Nielsen et al. in 1991. PNA is not found in nature and is artificially synthesized by chemical methods. PNA forms a duplex by its hybridization to a natural nucleic acid having a nucleotide sequence complementary thereto. When their lengths are equal, a PNA/DNA duplex is more stable than a DNA/DNA duplex, and a PNA/RNA duplex is more stable than a DNA/RNA duplex. Furthermore, since PNA has a single base mismatch that makes the duplex unstable, the ability of PNA to detect SNP (single nucleotide polymorphism) is better than that of natural nucleic acid. PNA is chemically stable and is also biologically stable because it is not degraded by nuclease or protease. Furthermore, PNA is one of substances that recognize genes, like LNA (locked nucleic acid) or MNA (morpholino nucleic acid), and has a backbone consisting of polyamide. PNA has advantages in that it has very high affinity and selectivity and is thermally and chemically highly stable so that it can be easily stored and cannot be readily degraded.

Accordingly, the present inventors have made extensive efforts to identify a Korea-specific nucleotide sequence by analyzing the nucleotide sequences of the glycoprotein (G) of VHSV isolates isolated from cultured *Paralichthys olivaceus* in Korea and phylogenetically comparing Korean VHSV isolates with previously reported Japanese and Chinese VHSV isolates, thereby providing useful data required for the surveillance, genetic diversity analysis, molecular dynamic characterization, monitoring and control of zoned aquatic organism diseases. As a result, the present inventors have found that when a genetic marker for determining the region-specific genotype of VHSV and a peptide nucleic acid (PNA) having a high binding affinity for the genetic marker DNA are used so as to exhibit different melting temperatures depending on the region-specific genotype, the region-specific genotype of VHSV can be determined in a simple, rapid and accurate manner, thereby completing the present invention.

DISCLOSURE OF INVENTION

Technical Problem

It is an object of the present invention to provide a probe that can determine a region-specific genotype of a target gene of VHSV, and a PNA probe comprising a reporter or a quencher, which is attached to both ends of the probe.

Another object of the present invention is to provide a kit for analyzing nucleotide polymorphism of VHSV, in which the kit comprises the above-described probe or PNA.

Still another object of the present invention is to provide a method for determining a region-specific genotype of VHSV, the method comprising a step of using the above-described probe or PNA.

Technical Solution

To achieve the above object, the present invention provides a probe for determining a region-specific genotype of viral hemorrhagic septicemia virus (VHSV), in which the probe is capable of hybridizing under strict conditions to a sequence fragment containing C755A and A756G single-nucleotide polymorphism mutations in the G-protein sequence of the VHSV.

The present invention also provides a PNA probe for determining a region-specific genotype of VHSV, the PNA probe comprising a reporter or a quencher, which is attached to both ends of the above-described probe.

The present invention also provides a kit for detecting single-nucleotide polymorphisms (SNPs) that determine a region-specific genotype of VHSV, in which the kit comprises the above-described probe or PNA.

The present invention also provides a method of detecting single-nucleotide polymorphisms (SNPs), which determine a region-specific genotype of VHSV, by use of a PNA, the method comprising the steps of: (a) isolating target DNA from the VHSV; (b) hybridizing the target DNA to the above-described probe; (c) obtaining a temperature-dependent melting curve while increasing the temperature of a hybridized product resulting from step (b); and (d) analyzing the obtained melting curve.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8 is a table in which melting temperatures ($T_m$) obtained from the melting curve graphs of PNA probes for various genotypes are summarized as genetic codes.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well-known and commonly employed in the art.

In the present invention, a single-nucleotide polymorphism marker for determining the genotype of viral hemorrhagic septicemia virus (VHSV) was selected in order to rapidly and conveniently analyze the geographical genotype of VHSV.

Figure 1:
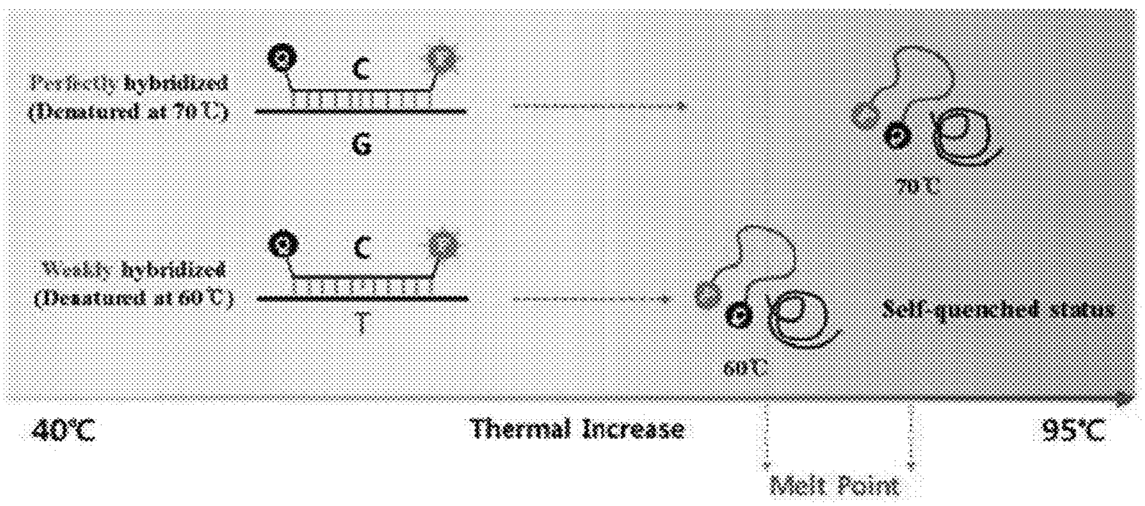
FIG. 1 is a conceptual view illustrating the technical characteristics of melting curve analysis employing a PNA for detecting single nucleotide polymorphisms (SNPs) that determine a region from which VHSV was isolated, according to a preferred embodiment of the present invention.
Figure 3:
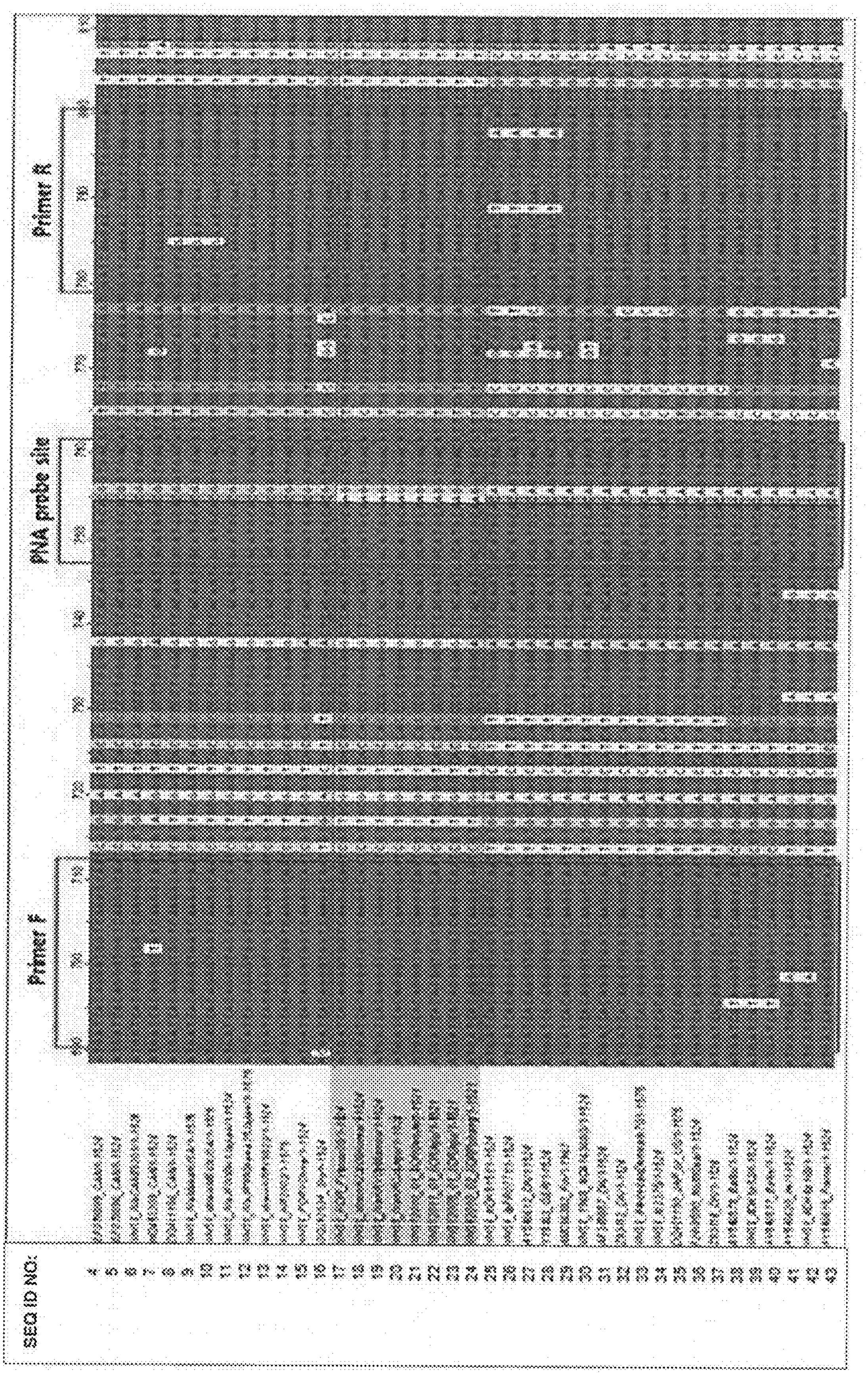
FIG. 3 is a sequence view (SEQ ID NOs: 4 to 43) illustrating a PNA binding site and the results of G-protein sequencing performed to determine a genotype identified for each region from which VHSV was isolated, according to the present invention.

Specifically, in order to determine the region-specific sequences of VHSV isolates isolated from aquatic organisms in various countries, the VHSV G-protein was sequenced. As a result, it was shown that Korean VHSV isolates indicated A at the $755^{th}$ base pair and G at the $756^{th}$ base pair, whereas VHSV isolates isolated from aquatic organisms in USA, Canada and Japan indicated C at the $755^{th}$ base pair and G at the $756^{th}$ base pair, and European VHSV isolates indicated C at the $755^{th}$ base pair and A at the $756^{th}$ base pair (FIGS. 1 and 3).

Figure 2:
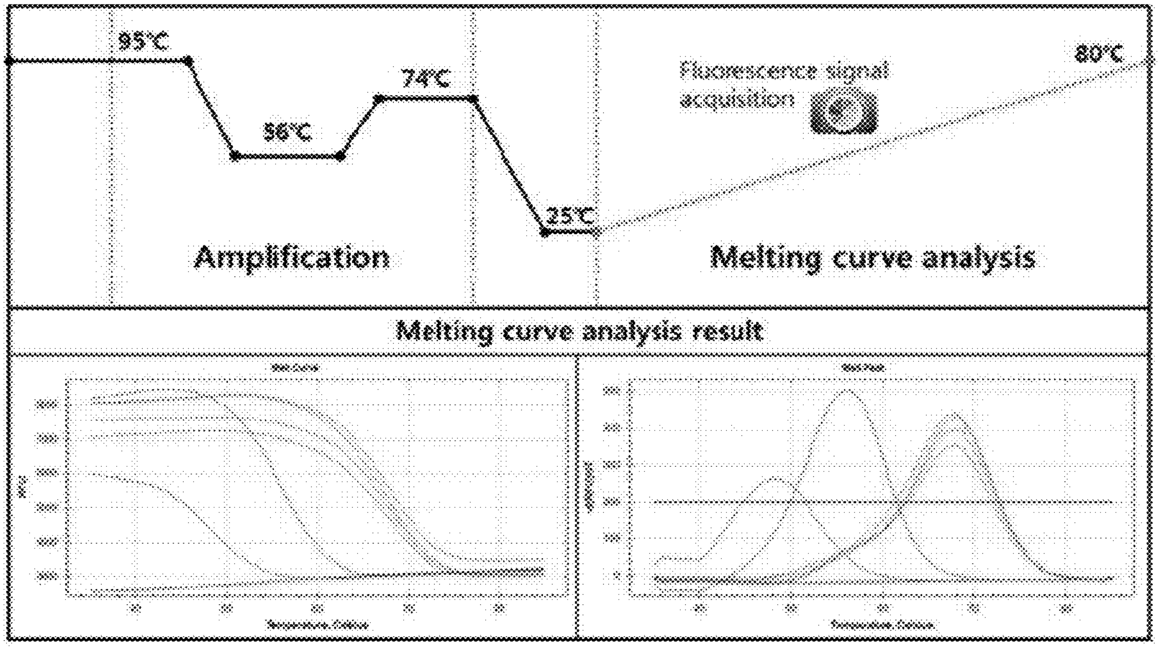
FIG. 2 is a schematic view illustrating a hybridization step and a step of obtaining a melting curve in a method of determining a genotype identified for each region from which VHSV was isolated, by use of PNA according to a preferred embodiment of the present invention.
Figure 4:
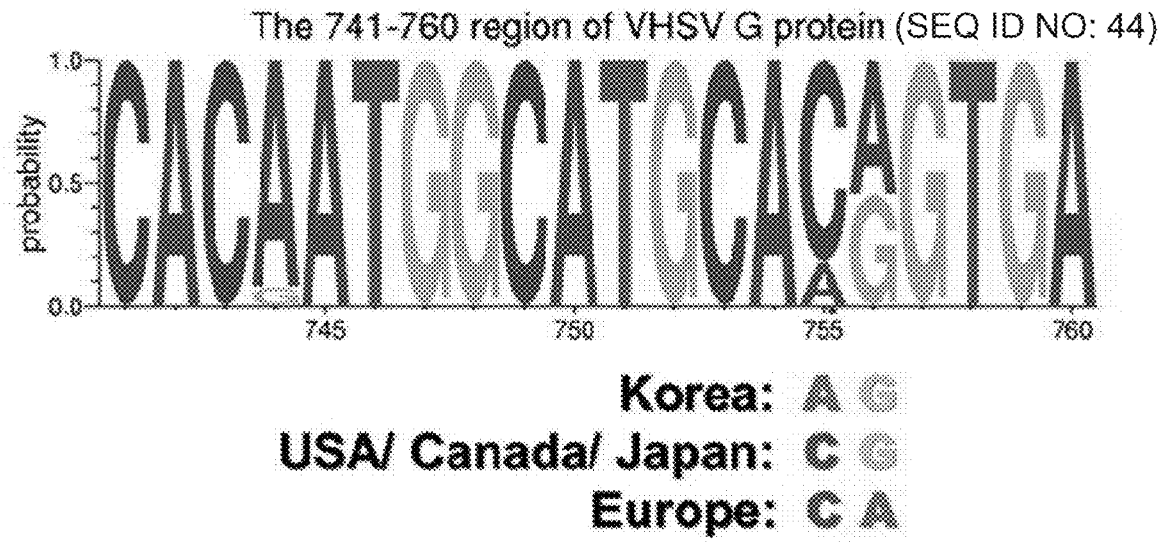
FIG. 4 is a gene position view (SEQ ID NO: 44) illustrating an example of a nucleotide mutation region included in PNA on the G-protein gene, which determines a genotype identified for each region from which VHSV was isolated, according to the present invention.

In other words, when PNA-DNA binding, which is stronger than DNA-DNA binding, was used, the PNA showed a difference in melting temperature ($T_m$) of about 10 to 15° C. even in the presence of one nucleotide mismatch. Using this characteristic, it was found that single-nucleotide polymorphism (SNP) mutations and changes of nucleotides in the insertion-deletion mutation (In/Del) of VHSV can be detected (FIGS. 2 and 4).

Therefore, in one aspect, the present invention is directed to a probe for determining a region-specific genotype of VHSV, in which the probe is capable of hybridizing under strict conditions to a sequence fragment containing C755A and A756G single-nucleotide polymorphism mutations in the G-protein sequence of viral hemorrhagic septicemia virus (VHSV).

In the present invention, the probe may consist of 5-20 nucleotides.

In the present invention, the probe may have, at positions 8 and 9, a sequence corresponding to a G-protein single-nucleotide polymorphism (SNP) site that determines the region-specific genotype of VHSV.

In the present invention, the probe may be represented by SEQ ID NO: 1.

In another aspect, the present invention is directed to a PNA probe having a reporter and a quencher, which are attached to both ends of the above-described probe. In other words, the PNA probe according to the present invention may have a reporter and a fluorescence quencher capable of quenching the fluorescence of the reporter, which are attached to both ends. In the present invention, the reporter may be one or more selected from the group consisting of FAM (6-carboxyfluorescein), Texas red, HEX (2',4',5',7',-tetrachloro-6-carboxy-4,7-dichlorofluorescein), JOE, Cy3, and Cy5. The quencher may be one or more selected from the group consisting of TAMRA (6-carboxytetramethyl-rhodamine), BHQ1, BHQ2 and Dabcyl, but is not limited thereto, and preferably Dabcyl can be used as the quencher.

Furthermore, a PNA may be analyzed using a hybridization method different from a hydrolysis method that is used to analyze a TaqMan probe, and probes having similar functions include a molecular beacon probe, a scorpion probe and the like.

FIG. 1 is a conceptual view illustrating the technical characteristics of a PNA for detecting single nucleotide polymorphisms (SNPs) that determine a genotype identified for each region from which VHSV originated, according to a preferred embodiment of the present invention. As shown therein, the PNA according to the present invention can generate a fluorescence signal after its hybridization to a target nucleic acid. As the temperature increases, the PNA is rapidly melted from the target nucleic acid at its suitable melting temperature ($T_m$), and thus the fluorescence signal is quenched. According to the present invention, through high-resolution fluorescence melting curve analysis (FMCA) based on a melting curve obtained from the fluorescence signal depending on this temperature change, the presence or absence of a nucleotide mutation in the target nucleic acid may be detected. If the PNA according to the present invention perfectly matches with the nucleotide sequence of the target nucleic acid, it then shows an expected melting temperature ($T_m$) value, but if the PNA mismatches with a target nucleic acid in which a nucleotide mutation is present, it shows a melting temperature ($T_m$) value lower than an expected value.

The present inventors comparatively analyzed genetic sites that determine genotypes identified for various regions from which VHSV originated, thereby constructing a PNA comprising a nucleotide sequence represented by SEQ ID NO: 1. Using this PNA, a melting curve was obtained from a VHSV DNA sample, and the melting temperature ($T_m$) of the probe was analyzed from the melting curve. As a result, as described in the Examples below, different results could be obtained for single-nucleotide polymorphisms (SNPs) that determine a genotype identified for each region from which VHSV originated. According to the present invention, the PNA having a high binding affinity for DNA is used so as to exhibit different melting temperatures ($T_m$) depending on single-nucleotide polymorphisms (SNPs) that determine a genotype identified for each region from which VHSV originated, whereby single-nucleotide polymorphisms (SNPs) that determine a genotype identified for each region from which VHSV originated can be detected in a simple, rapid and accurate manner.

In the present invention, although the length of the nucleotide sequence of the PNA is not particularly limited, the PNA may be constructed to have a length of 5- to 20-mer so as to contain single-nucleotide polymorphisms (SNP) that determine a genotype identified for each region from which VHSV originated.

In the present invention, a probe may be constructed to have a desired $T_m$ value by adjusting the length of the PNA, and even in the case of PNAs having the same length, the $T_m$ value may be adjusted by changing the nucleotide sequence. Furthermore, since a PNA has a binding affinity higher than a DNA probe, it generally has a higher $T_m$ value. Thus, the PNA can be constructed to have a length shorter than a DNA probe, so that it can detect even adjacent SNPs. In a conventional HRM (High Resolution Melt) method, the difference in $T_m$ value from a target nucleic acid is as low as about 0.5° C., and thus an additional analytic program or a minute change or correction in temperature is required, and for this reason, it is difficult to perform analysis, when two or more SNPs appear. However, the PNA according to the present invention is not influenced by the probe sequence and SNPs, and thus makes it possible to perform analysis in a simple and convenient manner.

In addition, for a difference in melting temperature ($T_m$) from a target nucleic acid having a nucleotide mutation, the PNA according to the present invention is preferably designed such that the position of a nucleotide mutation in a target nucleic acid corresponds to the central position of the target nucleic acid. When the nucleotide mutation is located at the central position of the probe, the probe structurally differs from the target nucleic acid, and the PNA binds to the target nucleic acid while forming a loop. Due to this structural difference, the probe shows a great difference in melting temperature ($T_m$).

For this reason, when the PNA according to the present invention comprises 16 to 17 nucleotides, it preferably has, a sequence corresponding to a single-nucleotide polymorphism (SNP) site, at one or more positions of the $8^{th}$ and $9^{th}$ positions. This PNA may have a structural modification by containing, at the central position thereof, a sequence corresponding to single-nucleotide polymorphisms (SNPs) that determine a genotype identified for each region from which VHSV originated, thereby further increasing the difference in melting temperature ($T_m$) from a target nucleic with which the probe perfectly matches.

Furthermore, the PNA for detecting single-nucleotide polymorphisms (SNPs) that determine the region-specific genotype of VHSV according to the present invention shows different melting temperatures ($T_m$) depending on nucleotide sequences (or SNP) to which it binds. Thus, two or more nucleotide sequences can be detected with one PNA (or probe), and two or more PNAs may be contained in one tube for use.

The PNA according to the present invention relates to a technology for determining the region-specific genotype of VHSV. Specifically, single-nucleotide polymorphisms in VHSV can be detected in a simple, rapid and accurate manner by hybridizing the PNA of the present invention to the target nucleic acid of VHSV and analyzing a melting curve resulting from the hybridization (FIG. 2).

Therefore, in still another aspect, the present invention is directed to a method of detecting single-nucleotide polymorphisms (SNPs), which determine a region-specific genotype of VHSV, by use of a PNA, the method comprising the steps of: (a) isolating target DNA from the VHSV; (b) hybridizing the target DNA to the above-described probe; (c) obtaining a temperature-dependent melting curve while increasing the temperature of a hybridized product resulting from step (b); and (d) analyzing the obtained melting curve.

In addition, the present invention is directed to a method of detecting single-nucleotide polymorphisms (SNPs), which determine a region-specific genotype of VHSV, by use of a PNA, the method comprising the steps of: (a) isolating target DNA from the VHSV; (b) hybridizing the target DNA to the above-described PNA; (c) obtaining a temperature-dependent melting curve while increasing the temperature of a hybridized product resulting from step (b); and (d) analyzing the obtained melting curve.

The step (b) of hybridizing the target DNA includes reacting the PNA according to the present invention with the DNA of VHSV. This step may include a PCR process, and can use a forward/reverse primer set for PCR. This hybridizing step and PCR conditions may include all various method well-known to a person having ordinary skill in the art (hereinafter referred to as 'PHOSITA'). In addition, the hybridizing step may include a melting process after the completion of the PCR.

In the present invention, the target DNA isolated from the VHSV may contain a single-nucleotide polymorphism (SNP) site in the G-protein gene. Generally, the G-protein-encoding gene which is expressed on the VHSV surface has a genotype enabling species discrimination and regional discrimination, and thus is effective as a marker for determining a region from which the virus originated.

Furthermore, the step of obtaining the temperature-dependent melting curve is performed to obtain the melting temperature ($T_m$) of the VHSV DNA sample. Specifically, a temperature-dependent change in fluorescence intensity can be obtained as the temperature-dependent melting curve by measuring the fluorescence intensity while increasing the temperature of the hybridized product. Namely, as the hybridization analysis method, FMCA (Fluorescence Melting Curve Analysis) may be used. The FMCA is a method of analyzing the difference in binding affinity between a PCR product and an added probe by $T_m$. For example, a $T_m$ value can be obtained by measuring the intensity of fluorescence using a general real-time PCR system while increasing the temperature by 1° C. for each time.

Then, the step of detecting the single-nucleotide polymorphisms (SNPs) that determines the genotype identified for each region from which the VHSV originated is a step of detecting the single-nucleotide polymorphisms (SNPs), which determine the genotype identified for each region from which the VHSV originated, based on the melting temperature of the obtained melting curve. For example, the melting temperature of the obtained melting curve may be compared with the previously known melting temperature of the single-nucleotide polymorphisms (SNPs) that determine the genotype identified for each region from which the VHSV originated, thereby detecting the single-nucleotide polymorphisms (SNPs) that determine the genotype identified for each region from which the VHSV originated. The melting curve obtained using the PNA according to the present invention have different melting temperatures ($T_m$) depending on single-nucleotide polymorphisms (SNPs) that determine a genotype identified for each region from which VHSV originated (FIG. 8). Using this difference in melting temperature, it is possible to detect single-nucleotide polymorphisms (SNPs) that determine a genotype identified for each region from which VHSV originated.

Figures 6, 7:
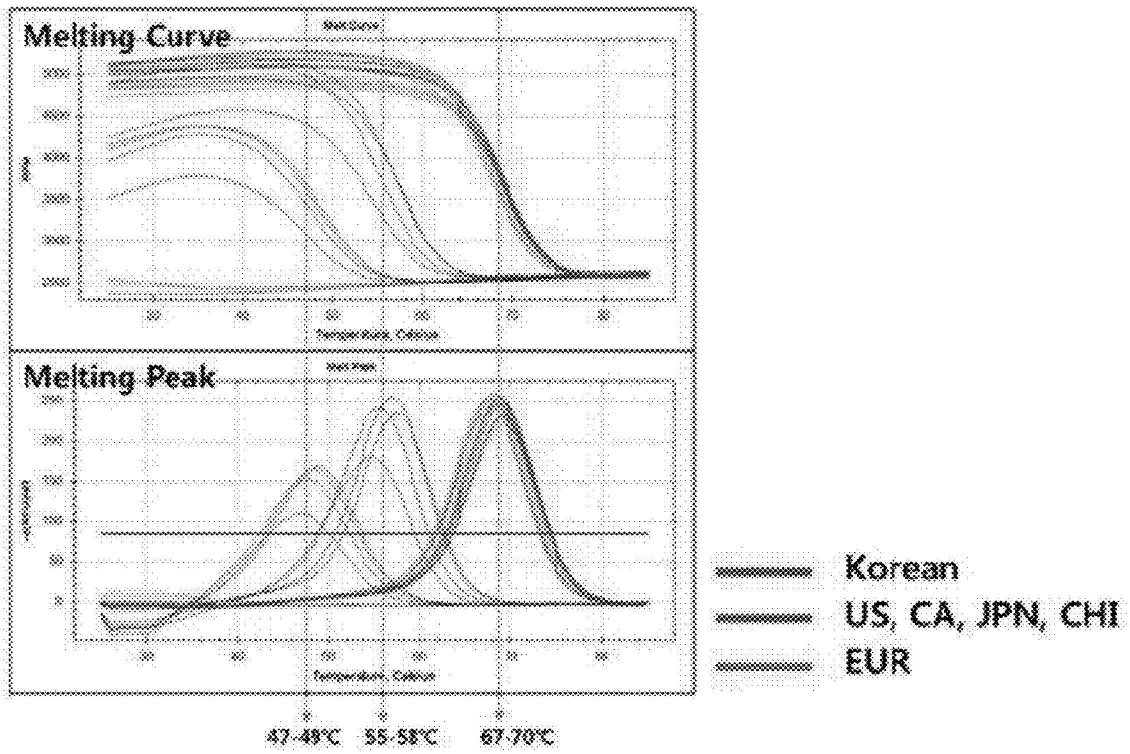
FIG. 6 shows real-time PCR reaction conditions for detecting single nucleotide polymorphisms (SNPs) that determine a genotype identified for each region from which VHSV was isolated, according to the present invention.
FIG. 7 is a graph showing the results of analyzing each genotype for detecting single nucleotide polymorphisms (SNPs) that determine a genotype identified for each region from which VHSV was isolated, according to the present invention.

FIG. 7 is a graph illustrating a step of obtaining a melting peak curve from a melting curve in a method for detecting single-nucleotide polymorphisms (SNPs), which determine a genotype identified for each region from which VHSV originated, by use of the PNA according to the present invention. As shown therein, using the slope value of the melting curve, a temperature-dependent melting peak curve can be obtained. This melting peak curve makes it easy to grasp the melting temperature ($T_m$) of single-nucleotide polymorphisms (SNPs) that determine a genotype identified for each region from which VHSV originated. To this end, the step of obtaining the temperature-dependent melting curve includes a step of obtaining a temperature-dependent melting peak curve from the obtained temperature-dependent melting curve, and the step of detecting the single-nucleotide polymorphisms (SNPs) that determines the genotype identified for each region from which the VHSV originated can detect the single-nucleotide polymorphisms (SNPs) that determine the genotype identified for each region from which the VHSV originated, based on a melting temperature of the obtained melting peak curve.

In yet another aspect, the present invention is directed to a kit for detecting single-nucleotide polymorphisms (SNPs) that determine a region-specific genotype of VHSV, the kit comprising the above-described probe or PNA.

In the present invention, the kit is a kit for analysis of nucleotide polymorphisms of multiple target DNAs or a single target DNA.

In the present invention, a probe of the kit may be a PNA.

The kit of the present invention may optionally include reagents required for performing a target nucleic acid amplification reaction (e.g., PCR reaction), such as buffer, DNA polymerase cofactor, and deoxyribonucleotide-5-triphosphate. In addition, the kit of the present invention may also comprise various polynucleotide molecules, a reverse transcriptase, various buffers and reagents, and an antibody that inhibits the activities of a DNA polymerase.

When the kit is used, a single nucleotide mutation and a mutation caused by nucleotide deletion or insertion in a target nucleic acid can be effectively detected by analysis of a melting curve obtained using the PNA, thereby detecting the single-nucleotide polymorphisms (SNPs) that determine the genotype identified for each region from which the VHSV originated.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1: Development of Single-Nucleotide Polymorphism (SNP) Marker Specific for Genotype Identified for Each Region from which VHSV Originated To determine the region-specific sequences of VHSV isolates isolated from aquatic organisms in various countries, the sequences of the full-length open reading frames (ORFs) of the G-gene, which have high sequence mutations, were amplified by PCR using a designed primer set of VHSVG-ORF-F1 (5'-ATGGAATGGAATACTTTTTCT-TGGTG-3') and VHS V-G-ORF-R1(5'-TCAGACCGTCT-GACTTCTGGAGAACTGC-3'), thereby obtaining 1524-bp PCR products. The PCR amplification product was cloned using a pGEM®-T Easy vector (Promega, USA) and purified using an Exprep™ Plasmid SV DNA prep kit (GeneAll Biotechnology Co., Ltd., Korea), and the purified plasmid DNA was sequenced.

The G-protein sequences of VHSVs isolated from various regions were aligned, and a gene sequence occurring specifically in Korean VHSV isolates was determined. It was shown that nucleotides making it possible to detect Korean VHSV isolates were the nucleotides at 755 bp and 756 bp of the VHSV G-protein gene. Specifically, the nucleotides are A (755 bp) and G (756 bp) in Korean VHSV isolates, C (755 bp) and G (756 bp) in VHSV isolates isolated from USA, Canada and Japan, and C and A in European VHSV isolates.

Example 2: Preparation of PNA for Determining Region-Specific Genotype of VHSV RNA extracted from VHSV was reverse-transcribed to synthesize cDNA. To perform PCR using the cDNA as a template, a G-protein primer pair was prepared.

Specifically, the G-protein gene of VHSV was sequenced, and the nucleotide sequences were compared with each other to identify a SNP showing significance for each region in which the VHSV occurred. Based on the SNPs, region-specific sequences were selected.

Figure 5:
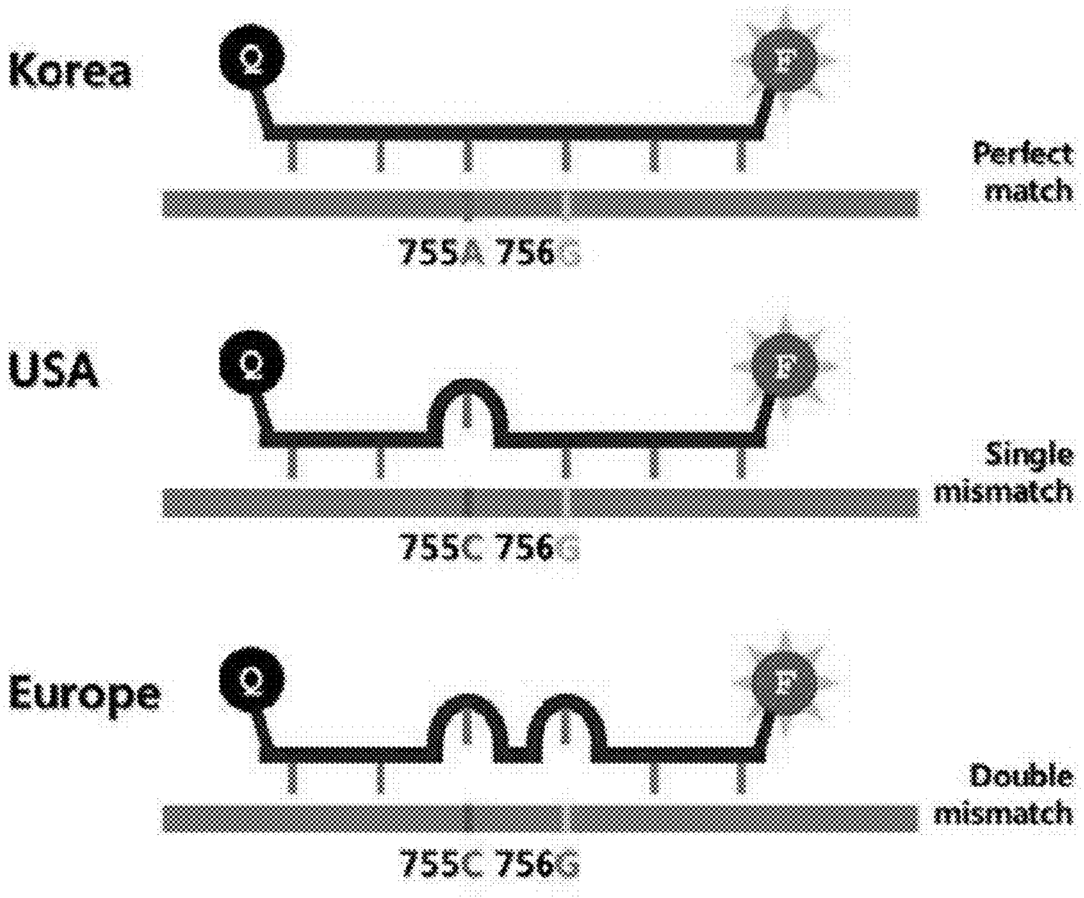
FIG. 5 is a schematic view illustrating an example of a method of detecting different degrees of hybridization to each probe according to a genotype and the G-protein binding position of a PNA for determining a genotype depending on each VHSV-isolated region according to the present invention.

FIG. 4 shows an example of the nucleotide sequences of a portion and SNP of the VHSV G-protein gene according to the present invention and a PNA probe derived therefrom, and FIG. 5 illustrates gene diversity indicating binding affinity between PNA probe and the binding sequence on the VHSV G-protein gene and the binding affinity of the PNA probe according to this. In FIG. 5, the degree of binding of the PNA probe to the residues at position 755 and 756, which are region-specific genetic sites, are indicated as "match" and "mismatch". As shown in FIG. 5, the number of mismatches enabled regional discrimination. Thus, a nucleotide sequence (SEQ ID NO: 1) having the positions at the center thereof was constructed as the nucleotide sequence of the PNA probe according to the present invention.

As described above, the nucleotide sequence of the PNA probe according to the present invention was determined. The nucleotide sequence is shown in Table 1 below.

TABLE 1

| SEQ ID NOs: | Name | Sequence (5'→3') | Remarks |
|---|---|---|---|
| SEQ ID NO: 1 | VHSV-1 | Dabcyl-GCATGCAAGGTGAC-O-K(HEX) | PNA |

In Table 1, O represents a linker, and K represents lysine.

In order to make it possible to measure the fluorescence of the PNA probe, HEX was attached to the PNA probe.

Next, as shown in Table 1 above, the PNA probe according to the present invention was constructed using the nucleotide sequence, a reporter and a quencher. The PNA probe was designed using a PNA probe designer (Appliedbiosystems, USA). All the PNA probes used in the present invention were synthesized using a HPLC purification method by Panagene (Korea). The purities of all the synthesized probes were analyzed by mass spectrometry, and the unnecessary secondary structures of the probes were avoided for effective binding to target nucleic acids.

Example 3: Melting Curve Analysis for VHSV Sample

Using the PNA probe constructed according to Examples 1 and 2 above, a melting curve for a cDNA sample from VHSV isolated from each region was obtained and analyzed to detect single-nucleotide polymorphisms (SNPs) that determine the region-specific genotype of VHSV.

PCR was performed using CFX96™ Real-Time system (Bio-Rad Laboratories Inc., USA) under asymmetric PCR conditions in order to produce single-stranded target nucleic acids. The asymmetric PCR conditions were as follows. Three probes (0.5 μl of PNA probe constructed in Example 1, 0.05 μM forward primer, and 0.5 μM reverse primer (asymmetric PCR, Table 2)) and 0.5 μl of *Streptococcus*

*iniae* DNA were added to 1× SeaSunBio Real-Time FMCA™ buffer (SeasunBio, Korea), 2.5 mM $MgCl_2$, 200 μM dNTPs, and 1.0 U Taq polymerase to a total volume of 20 μl, and then real-time PCR was performed.

TABLE 2

| SEQ ID NOs: | Primer name | Sequence (5'→3') |
|---|---|---|
| SEQ ID NO: 2 | VHSV-F1 | GATCACAGGGTGGTCAAGGCAA |
| SEQ ID NO: 3 | VHSV-R1 | TCCCCCAGGTCGGTCTTGATC |

FIG. 6 is a table showing temperature and time conditions in a process of amplifying the G-protein region of a VHSV cDNA sample according to the Example of the present invention, hybridizing the PNA probe, constructed according to Examples 1 and 2, to the amplified product, and increasing the temperature of the hybridized product. As shown FIG. 6, the real-time PCR process was performed under the following conditions: denaturation at 95° C. for 5 min, and then repetition of 40 cycles, each consisting of 95° C. for 30 sec, 56° C. for 45 sec, and 74° C. for 30 sec. Melting curve analysis was performed under the following conditions: denaturation at 95° C. for 5 min, and then progress of stepwise hybridization starting from 85° C. to 25° C., followed by fluorescence measurement while temperature rises from 25° C. to 85° C. at a rate of 1° C. A stop state was maintained for 10 sec between each step.

As shown in FIG. 7, melting curves were measured in one tube, and the number of graph lines for each melting curve represents measured values for different samples. As can be seen therein, the melting curve obtained using the PNA according to the present invention had different melting temperatures ($T_m$) depending on regions from which VHSV was isolated.

FIG. 8 is a table comparing the results from the temperature-dependent melting curve graph with the results of sequencing that is a standard method for analysis of single-nucleotide polymorphisms.

As shown herein, the use of the PNA probe according to the present invention showed consistent melting temperatures depending on regions from which VHSV was isolated, indicating that the use of the PNA probe according to the present invention makes it possible to detect single-nucleotide polymorphisms (SNPs) that determine the region-specific genotype of VHSV.

When unknown VHSV cDNA sample species are to be discriminated using the PNA probe according to the present invention, melting temperature-dependent types as shown in FIG. 8 may be preset and used.

Specifically, a peak of about 69° C. in $T_m$ values obtained by performing melting curve analysis as described in Example 2 was regarded as a perfect match, a peak of about 58° C. was regarded as a single mismatch, and a peak of about 49° C. was regarded as a double mismatch. Based on the analysis results, Korean VHSV isolates were coded as a perfect match, USA, Canadian, Japanese and Chinese VHSV isolates were coded as a single mismatch, and European VHSV isolates were coded as a double mismatch, such that each isolate had a characteristic value.

INDUSTRIAL APPLICABILITY

The PNA probe having a high binding affinity for DNA according to the present invention can be used to exhibit different melting temperatures depending on genotypes identified for each region from which the VHSV originated, whereby a genotype marker of identified for each region from which the VHSV originated can be determined in a simple, rapid and accurate manner.

In addition, the PNA for determining the region-specific genotype of VHSV according to the present invention may have a structural modification by comprising, at the central position thereof, a sequence corresponding to single-nucleotide polymorphisms (SNPs) that determine a genotype for each region from which VHSV originated, whereby the difference in melting temperature ($T_m$) from a target nucleic acid with which the PNA perfectly matches can further be increased.

Furthermore, the PNA for detecting single-nucleotide polymorphisms (SNPs) that determine the region-specific genotype of VHSV according to the present invention shows different melting temperatures ($T_m$) depending on nucleotide sequences (or SNP) to which it binds. Thus, two or more nucleotide sequences can be detected with one PNA (or probe), and two or more PNAs may be contained in one tube for use.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method of detecting single-nucleotide polymorphisms (SNPs), which determine a region-specific genotype of viral hemorrhagic septicemia virus (VHSV), to identify a geographic region of origin of a VHSV isolate distinguished from other geographic regions of origin of VHSV, using a single probe which is effective for identifying VHSV in all such geographic regions, the method comprising the steps of:

(a) synthesizing target DNA by reverse transcribing RNA extracted from the VHSV isolate;

(b) hybridizing the target DNA to a PNA probe which has a nucleobase sequence consisting of the nucleobase sequence set forth in SEQ ID NO: 1 and a reporter and/or a quencher attached to the PNA probe, which is capable of hybridizing under strict conditions to a sequence fragment having C755A and A756G single-nucleotide polymorphism mutations in the G-protein sequence of the VHSV isolate;

(c) obtaining a temperature-dependent melting curve while increasing the temperature of a hybridized product resulting from step (b); and (d) analyzing the obtained melting curve to identify the geographic region of origin of the VHSV isolate, wherein the melting peak of the melting curve correlates to the origin of the VHSV isolate and distinguishes that the isolate originated from either (i) Korea, (ii) USA, Canada, Japan, or China, or (iii) Europe.

2. The method of claim 1, wherein both a reporter and a quencher are attached to the PNA probe, and the reporter is attached to one end of the probe and the quencher is attached to the other end of the probe.

3. The method of claim 2, wherein the reporter is one or more selected from the group consisting of FAM (6-carboxyfluorescein), Texas red, HEX (2', 4', 5', 7',-tetrachloro-6-carboxy-4,7-dichlorofluorescein), JOE, Cy3, and Cy5.

4. The method of claim 2, wherein the quencher is one or more selected from the group consisting of TAMRA (6-carboxytetramethyl-rhodamine), BHQ1, BHQ2 and Dabcyl.

* * * * *